United States Patent
Hurley et al.

(10) Patent No.: US 10,172,728 B2
(45) Date of Patent: Jan. 8, 2019

(54) TRANSTIBIAL PROSTHETIC SOCKET WITH TEXTILE JACKET

(71) Applicant: LIM Innovations, Inc., San Francisco, CA (US)

(72) Inventors: Garrett Ray Hurley, San Francisco, CA (US); Juan Jacobo Cespedes, San Francisco, CA (US); Jesse Robert Williams, San Francisco, CA (US); Preston Fung, South San Francisco, CA (US); Monica Ha, San Francisco, CA (US)

(73) Assignee: LIM Innovations, Inc., San Francisco, CA (US)

( * ) Notice: Subject to any disclaimer, the term of this patent is extended or adjusted under 35 U.S.C. 154(b) by 0 days.

(21) Appl. No.: 15/360,559

(22) Filed: Nov. 23, 2016

(65) Prior Publication Data

US 2017/0143520 A1    May 25, 2017

Related U.S. Application Data

(60) Provisional application No. 62/259,931, filed on Nov. 25, 2015, provisional application No. 62/287,702, (Continued)

(51) Int. Cl.
  *A61F 2/50* (2006.01)
  *A61F 2/60* (2006.01)
  (Continued)

(52) U.S. Cl.
  CPC .................. *A61F 2/80* (2013.01); *A61F 2/60* (2013.01); *A61F 2/78* (2013.01); *A61F 2/7812* (2013.01);
  (Continued)

(58) Field of Classification Search
  CPC .... A61F 2/50; A61F 2/60; A61F 2/601; A61F 2/602; A61F 2/76; A61F 2/78;
  (Continued)

(56) References Cited

U.S. PATENT DOCUMENTS 1,144,681 A    6/1915    Apgar
1,893,853 A    1/1933    Tullis
(Continued)

FOREIGN PATENT DOCUMENTS

DE    319623    3/1920
EP    204407    12/1986
(Continued)

OTHER PUBLICATIONS

Allard USA, "Cut-4-Custom: Custom TLSO in Less Than an Hour," O&P Edge Magazine, downloaded from the internet: <URL: http://www.oandp.com/articles/news_2010-07-01_24.asp>, 2 pages, Jul. 2010.
(Continued)

*Primary Examiner* — Thomas Sweet
*Assistant Examiner* — Christie L Bahena
(74) *Attorney, Agent, or Firm* — Gordon & Jacobson, P.C.

(57) ABSTRACT

A transtibial prosthetic socket frame may include a distal base assembly having a base plate, a carriage configured to support a socket suspension arrangement, and a distal prosthetic component connector. The distal base assembly supports a set of struts that includes two anterior struts and a single posterior strut. The set of struts and distal base assembly collectively define a prosthetic socket cavity having a central longitudinal axis and a residual limb hosting volume. The distal prosthetic component connector has a connecting adapter that is rotatable with respect to the prosthetic socket, and moveable with respect to the base
(Continued)

plate between being aligned with the prosthetic socket's central longitudinal axis and a position offset therefrom.

23 Claims, 35 Drawing Sheets

Related U.S. Application Data filed on Jan. 27, 2016, provisional application No. 62/305,477, filed on Mar. 8, 2016.

(51) Int. Cl.
*A61F 2/78* (2006.01)
*A61F 2/80* (2006.01)

(52) U.S. Cl.
CPC ...... *A61F 2/7843* (2013.01); *A61F 2002/503* (2013.01); *A61F 2002/509* (2013.01); *A61F 2002/5012* (2013.01); *A61F 2002/5018* (2013.01); *A61F 2002/5021* (2013.01); *A61F 2002/5027* (2013.01); *A61F 2002/5032* (2013.01); *A61F 2002/5052* (2013.01); *A61F 2002/5053* (2013.01); *A61F 2002/607* (2013.01); *A61F 2002/608* (2013.01); *A61F 2002/7862* (2013.01); *A61F 2002/7875* (2013.01); *A61F 2002/802* (2013.01)

(58) Field of Classification Search
CPC .. A61F 2/7812; A61F 2/80; A61F 2002/5016; A61F 2002/5021; A61F 2002/5023; A61F 2002/5026; A61F 2002/5027; A61F 2002/5053; A61F 2002/5055; A61F 2002/5056; A61F 2002/607; A61F 2002/608; A61F 2002/7875; A61F 2002/802; A61F 2002/805
See application file for complete search history.

(56) References Cited

U.S. PATENT DOCUMENTS

| | | |
|---|---|---|
| 2,025,835 A | 12/1935 | Trautman |
| 2,229,728 A * | 1/1941 | Eddels .................. A61F 2/80 623/36 |
| 2,634,424 A | 4/1953 | O'Gorman |
| 2,759,271 A | 8/1956 | Von Duyke |
| 2,908,016 A | 10/1959 | Botko |
| 2,949,674 A | 8/1960 | Wexler |
| 3,678,587 A | 7/1972 | Madden |
| 4,161,042 A | 7/1979 | Cottingham et al. |
| 4,225,982 A | 10/1980 | Cochrane et al. |
| 4,268,922 A * | 5/1981 | Marsh .................. A61F 2/60 623/27 |
| 4,300,245 A | 11/1981 | Saunders |
| 4,459,709 A | 7/1984 | Leal et al. |
| 4,704,129 A | 11/1987 | Massey |
| 4,715,124 A | 12/1987 | Harrington |
| 4,778,717 A * | 10/1988 | Fitchmun ............. A43B 17/003 442/261 |
| 4,783,293 A | 11/1988 | Wellershaus et al. |
| 4,842,608 A | 6/1989 | Marx et al. |
| 4,872,879 A | 10/1989 | Shamp |
| 4,921,502 A | 5/1990 | Shamp |
| 4,988,360 A | 1/1991 | Shamp |
| 5,003,969 A | 4/1991 | Azer et al. |
| 5,014,441 A | 5/1991 | Pratt |
| 5,108,456 A | 4/1992 | Coonan, III |
| 5,116,382 A | 5/1992 | Steinkamp et al. |
| 5,133,777 A | 7/1992 | Arbogast et al. |
| 5,168,635 A | 12/1992 | Hoffman |
| 5,201,773 A | 4/1993 | Carideo, Jr. |
| 5,201,775 A | 4/1993 | Arbogast et al. |
| 5,246,464 A | 9/1993 | Sabolich |
| 5,312,669 A | 5/1994 | Bedard |
| 5,387,245 A | 2/1995 | Fay et al. |
| 5,431,624 A | 7/1995 | Saxton et al. |
| 5,503,543 A | 4/1996 | Laghi |
| 5,520,529 A | 5/1996 | Heckel |
| 5,529,575 A | 6/1996 | Klotz |
| 5,529,576 A | 6/1996 | Lundt et al. |
| 5,651,792 A | 7/1997 | Telikicherla |
| 5,652,053 A | 7/1997 | Liegeois |
| 5,718,925 A | 2/1998 | Kristinsson et al. |
| 5,728,165 A | 3/1998 | Brown, Sr. |
| 5,800,565 A | 9/1998 | Biedermann |
| 5,824,111 A | 10/1998 | Schall et al. |
| 5,885,509 A | 3/1999 | Kristinsson |
| 5,888,215 A | 3/1999 | Roos et al. |
| 5,888,217 A | 3/1999 | Slemker |
| 5,944,679 A | 8/1999 | DeToro |
| 6,033,440 A | 3/2000 | Schall et al. |
| 6,051,026 A | 4/2000 | Biedermann |
| 6,206,932 B1 | 3/2001 | Johnson |
| 6,228,124 B1 | 5/2001 | Slemker et al. |
| 6,231,618 B1 | 5/2001 | Schall et al. |
| D453,591 S | 2/2002 | Garden |
| 6,368,357 B1 | 4/2002 | Schon et al. |
| 6,444,282 B1 | 9/2002 | Shirer |
| 6,458,163 B1 | 10/2002 | Slemker et al. |
| 6,497,028 B1 | 12/2002 | Rothschild et al. |
| 6,500,210 B1 | 12/2002 | Sabolich et al. |
| 6,576,022 B2 | 6/2003 | Meyer et al. |
| 6,669,736 B2 | 12/2003 | Slemker et al. |
| 6,700,563 B1 | 3/2004 | Koizumi |
| 6,761,743 B1 | 7/2004 | Johnson |
| 6,767,332 B1 | 7/2004 | Pardue |
| 6,942,703 B2 | 9/2005 | Carstens |
| 6,974,484 B2 | 12/2005 | Caspers |
| 7,090,700 B2 | 8/2006 | Curtis |
| 7,105,122 B2 | 9/2006 | Karason |
| 7,172,714 B2 | 2/2007 | Jacobson |
| 7,240,414 B2 | 7/2007 | Taylor, Sr. |
| 7,300,466 B1 | 11/2007 | Martin |
| 7,318,504 B2 | 1/2008 | Vitale et al. |
| 7,338,532 B2 | 3/2008 | Haberman et al. |
| 7,344,567 B2 | 3/2008 | Slemker |
| 7,402,265 B2 | 7/2008 | Jacobson |
| 7,479,163 B2 | 1/2009 | Slemker et al. |
| 7,591,857 B2 | 9/2009 | Slemker et al. |
| 7,658,720 B2 | 2/2010 | Johnson, III |
| 7,753,866 B2 | 7/2010 | Jackovitch |
| 7,762,973 B2 | 7/2010 | Einarsson et al. |
| 7,980,921 B2 | 7/2011 | Saravanos |
| 7,985,192 B2 | 7/2011 | Sheehan et al. |
| 8,083,807 B2 | 12/2011 | Auberger et al. |
| 8,088,320 B1 | 1/2012 | Bedard |
| 8,116,900 B2 | 2/2012 | Slemker et al. |
| 8,142,517 B2 | 3/2012 | Horie |
| 8,303,527 B2 | 11/2012 | Joseph |
| 8,323,353 B1 | 12/2012 | Alley et al. |
| 8,382,852 B2 | 2/2013 | Laghi |
| 8,403,993 B2 | 3/2013 | Aram et al. |
| 8,465,445 B2 | 6/2013 | George |
| 8,470,050 B2 | 6/2013 | Dillingham |
| 8,535,389 B2 | 9/2013 | McKinney |
| 8,576,250 B2 | 11/2013 | Sabiston et al. |
| 8,894,719 B2 | 11/2014 | Egilsson et al. |
| D723,163 S | 2/2015 | Gottlieb |
| 8,978,224 B2 | 3/2015 | Hurley et al. |
| 9,044,349 B2 | 6/2015 | Hurley et al. |
| 9,155,636 B1 | 10/2015 | Fikes |
| 9,265,629 B2 | 2/2016 | Kelley et al. |
| 9,345,590 B2 | 5/2016 | Arabian et al. |
| 9,468,542 B2 | 10/2016 | Hurley et al. |
| 9,468,543 B2 | 10/2016 | Hurley et al. |
| 9,474,633 B2 | 10/2016 | Williams et al. |
| 9,549,828 B2 | 1/2017 | Hurley et al. |
| D778,452 S | 2/2017 | Cespedes et al. |
| 2002/0099450 A1 | 7/2002 | Dean, Jr. et al. |
| 2003/0181990 A1 | 9/2003 | Phillips |
| 2003/0233151 A1 * | 12/2003 | Lund .................. A61F 2/78 623/36 |

(56) References Cited

U.S. PATENT DOCUMENTS

| | | |
|---|---|---|
| 2004/0158332 A1 | 8/2004 | Carstens |
| 2004/0204771 A1 | 10/2004 | Swanson, Sr. |
| 2004/0260402 A1 | 12/2004 | Baldini et al. |
| 2005/0267600 A1* | 12/2005 | Haberman ............... A61F 2/76 623/38 |
| 2006/0009860 A1 | 1/2006 | Price, Jr. |
| 2006/0020348 A1 | 1/2006 | Slemker et al. |
| 2006/0020349 A1 | 1/2006 | Slemker |
| 2007/0004993 A1 | 1/2007 | Coppens et al. |
| 2007/0078523 A1 | 4/2007 | Kholwadwala et al. |
| 2007/0152379 A1 | 7/2007 | Jacobson |
| 2007/0298075 A1 | 12/2007 | Borgia et al. |
| 2008/0269914 A1 | 10/2008 | Coppens et al. |
| 2009/0036999 A1 | 2/2009 | Egilsson et al. |
| 2009/0076625 A1 | 3/2009 | Groves et al. |
| 2009/0105844 A1 | 4/2009 | Ortiz |
| 2009/0240344 A1 | 9/2009 | Colvin et al. |
| 2009/0299490 A1 | 12/2009 | Summit |
| 2010/0016772 A1 | 1/2010 | DeToro et al. |
| 2010/0036300 A1 | 2/2010 | Sheehan et al. |
| 2010/0036505 A1 | 2/2010 | Hassler |
| 2010/0082116 A1 | 4/2010 | Johnson et al. |
| 2010/0160722 A1 | 6/2010 | Kuyava et al. |
| 2010/0274364 A1 | 10/2010 | Pacanowsky et al. |
| 2011/0029096 A1 | 2/2011 | Laghi |
| 2011/0071647 A1* | 3/2011 | Mahon ................. A61F 2/5046 623/33 |
| 2011/0114635 A1 | 5/2011 | Sheehan et al. |
| 2011/0160871 A1 | 6/2011 | Boone et al. |
| 2011/0232837 A9 | 9/2011 | Ottleben |
| 2011/0320010 A1 | 12/2011 | Vo |
| 2012/0022667 A1 | 1/2012 | Accinni et al. |
| 2012/0041567 A1 | 2/2012 | Cornell |
| 2012/0101417 A1 | 4/2012 | Joseph |
| 2012/0101597 A1 | 4/2012 | Bache |
| 2012/0143077 A1 | 6/2012 | Sanders et al. |
| 2012/0165956 A1 | 6/2012 | Li |
| 2012/0191218 A1 | 7/2012 | McCarthy |
| 2012/0215324 A1 | 8/2012 | King |
| 2012/0253475 A1 | 10/2012 | Kelley et al. |
| 2012/0271210 A1 | 10/2012 | Galea et al. |
| 2012/0271214 A1 | 10/2012 | Blanck |
| 2012/0271433 A1 | 10/2012 | Galea et al. |
| 2012/0293411 A1 | 11/2012 | Leithinger |
| 2012/0296247 A1* | 11/2012 | Streeter ..................... A61F 2/68 602/5 |
| 2013/0123940 A1 | 5/2013 | Hurley et al. |
| 2013/0192071 A1 | 8/2013 | Esposito et al. |
| 2013/0197318 A1 | 8/2013 | Herr et al. |
| 2013/0245785 A1 | 9/2013 | Accini et al. |
| 2013/0267878 A1* | 10/2013 | Franke ................. A61F 5/0111 602/7 |
| 2013/0282141 A1 | 10/2013 | Herr et al. |
| 2014/0005798 A1* | 1/2014 | Bache ..................... A61F 2/80 623/33 |
| 2014/0005801 A1 | 1/2014 | Van der Watt et al. |
| 2014/0031953 A1 | 1/2014 | Mackenzie |
| 2014/0121783 A1* | 5/2014 | Alley ....................... A61F 2/76 623/33 |
| 2014/0149082 A1 | 5/2014 | Sanders et al. |
| 2014/0180185 A1 | 6/2014 | Zachariasen |
| 2014/0277584 A1 | 9/2014 | Hurley et al. |
| 2014/0277585 A1 | 9/2014 | Kelley et al. |
| 2014/0379097 A1 | 12/2014 | Hurley et al. |
| 2015/0168943 A1 | 6/2015 | Hurley et al. |
| 2015/0190252 A1 | 7/2015 | Hurley et al. |
| 2015/0265434 A1 | 9/2015 | Hurley et al. |
| 2015/0352775 A1 | 12/2015 | Geshlider et al. |
| 2016/0000587 A1 | 1/2016 | Hurley et al. |
| 2016/0022466 A1 | 1/2016 | Pedtke et al. |
| 2016/0058584 A1 | 3/2016 | Cespedes et al. |
| 2016/0143752 A1 | 5/2016 | Hurley et al. |
| 2016/0235560 A1 | 8/2016 | Cespedes et al. |
| 2016/0334780 A1 | 11/2016 | Dair et al. |
| 2017/0027718 A1 | 2/2017 | Williams et al. |
| 2017/0027720 A1 | 2/2017 | Pedtke et al. |
| 2017/0079811 A1 | 3/2017 | Kelley et al. |

FOREIGN PATENT DOCUMENTS

| | | |
|---|---|---|
| EP | 1433447 | 6/2004 |
| GB | 127451 | 6/1919 |
| GB | 2080114 | 2/1982 |
| WO | 1991016019 | 10/1991 |
| WO | 1998012994 | 4/1998 |
| WO | 2000003665 | 1/2000 |
| WO | 2000020572 | 6/2000 |
| WO | 2007035875 | 3/2007 |
| WO | 2008116025 | 9/2008 |
| WO | 2009093020 | 7/2009 |
| WO | 2012021823 | 2/2012 |
| WO | 2014004709 | 1/2014 |
| WO | 2014068269 | 5/2014 |

OTHER PUBLICATIONS

Alley, "The high-fidelity interface: Skeletal stabilization through alternating soft tissue compression and release," Myoelectric Symposium, Aug. 14-19, 2011 (3 pages).

Andrysek, "Lower-limb prosthetic technologies in the developing world: a review of literature from 1994-2010," Prosthetics and orthotics international, 34(4):378-398, Dec. 1, 2010.

Burgess et al., "The Management of Lower-Extremity Amputation: Surgery: Immediate Postsurgical Prosthetic Fitting: Patient Care," Superintendent of Documents, U.S. Government Printing Office, Washington D.C., publication prepared for the Prosthetic and Sensory Aids Service Dept of Medicine and Surgery, Veterans Administration, Aug. 1969 (129 pages).

Comfil (thermoformable composite technique). Fillauer Fabrication Manuel. Jun. 15, 2012.

Compton et al., "New plastics for forming directly on the patient*," Prosthetics and orthotics international, 2(1):43-47, Apr. 1978.

Conn, "Materials Science: A look At Some of the Substances on the Market for Device Fabrication," O&P Almanac, pp. 28-31, Jun. 2012.

Fairley, "From Academia to the Developing World," downloaded from <http://www.oandp.com/articles/2011-05_03.asp>, The O&P Edge, 5 pages, May 2011.

Fairley, "M.A.S. Socket: A Transfemoral Revolution," downloaded from <http://www.oandp.com/articles/2004-06_03.asp>, The O&P Edge, 3 pages, Jun. 2004.

Fairley, "Socket can be fabricated, modified, fitted-in one hour," downloaded from <http://www.oandp.com/articles/2007-06_09.asp>, The O&P Edge, 3 pages, Jun. 2007.

Fillauer LLC and Centri® "Comfil® Thermo Formable Composite Technique" Fillauer Fabrication Manuel, 14 pages, Jun. 15, 2012.

Gard, "Overview of Lower Limb Prosthetics Research," WRAMC and the VA Orthopedic & Prosthetic Workshop, Arlington, VA, 49 slides, Nov. 17, 2003.

Geil, "Consistency, precision, and accuracy of optical and electromagnetic shape-capturing systems for digital measurement of residual-limb anthropometrics of persons with transtibial amputation," J Rehabil Res Dev., 44 (4):515-524, May 20, 2007.

Gerschutz et al., "Mechanical Evaluation of Direct Manufactured Prosthetic Sockets," American Academy of Orthotists & Prosthetists, 38th Academy Annual Meeting and Scientific Symposium, USA, <URL: http://oandp.org/publications/iop/2012/2012-19.pdf>, 1 pages, Mar. 21, 2012.

Gleave, "A plastic socket and stump casting technique for above-knee prostheses," J Bone Joint Surg Br., 47:100-103, Feb. 1965.

Greenwald et al., "Volume Management: Smart Variable Geometry Socket (SVGS) Technology for Lower-Limb Prostheses," JPO: Journal of Prosthetics and Orthotics, 15(3):107-112, Jul. 1, 2003.

Hanger Inc., "ComfortFlex Socket System," downloaded from http://www.hanger.com/prosthetics/services/Technology/Pages/ComfortFlex.aspx, 2 pages, archived Sep. 17, 2012.

(56) References Cited

OTHER PUBLICATIONS

Hanger Prosthetics & Orthotics [online] "ComfortFlex Socket System," downloaded from the internet: <URL: http://www.hanger.com/prosthetics/services/Technology/Pages/ComfortFlex.aspx> on Nov. 28, 2012, 2 pages.
Hong et al., "Dynamic moisture vapor transfer through textiles part I: clothing hygrometry and the influence of fiber type," Textile Research Journal, 58(12):697-706, Dec. 1, 1988 [abstract only].
Hwang [designer], "Blooming Winner-Spark!" Spark Galleries, 3 pages, 2012.
Instamorph, "Moldable Plastic: Instructions" downloaded from URL: <http://www.instamorph.com/instructions>, 2 pages, archived Dec. 24, 2011.
Instamorph: "Remoldable prosthetics"; Apr. 2013, <www.instamorph.com/ideas/outdoors-and-ergonomics/remoldable-prosthetics>.
Jana, "Designing a cheaer, simpler prosthetic arm," ZDNet [online], <URL: http://www.zdnet.com/article/designing-a-cheaper-simpler-prosthetic-arm/> 3 pages, Nov. 14, 2011.
Koike et al., "The TC double socket above-knee prosthesis," Prosthet Orthot Int., 5(3):129-134, Dec. 1981.
Krouskop et al., "Computer-aided design of a prosthetic socket for an above-knee amputee," J Rehabil Res Dev., 24 (2):31-38, 1987.
Manucharian, "An investigation of comfort level trend differences between the hands-on patellar tendon bearing and hands-off hydrocast transtibial prosthetic sockets," J Prosthet Orthot., 23(3):124-140, Jul. 1, 2011.
Ottobock, "Initial and interim prostheses" Prosthetics Lower Extremities 2008, downloaded from the internet: <URL:http://www.ottobockus.com/cps/rde/xbcr/ob_us_en/08cat_4.pdf> on Feb. 2013, pp. 24-26.
Ottobock, "PU Resin Kit Polytol®" downloaded from the internet: <URL: http://www.ottobock.com/cps/rde/xchg/ob_com_en/hs.xsl/17414.html> on Dec. 17, 2012, 2 pages.

Quigley, "Prosthetics Management: Overview, Methods and Materials," Chapter 4, Atlas of Limb Prosthetics: Surgical, Prosthetic, and Rehabilitation Principles, (Second Edition), 19 pages, 1992.
Sanders et al., "Residual limb volume change: Systematic review of measurement and management," J Rehabil Res Dev., 48(8):949-986, 2011.
Sathishkumar et al., "A cost-effective, adjustable, femoral socket, temporary prosthesis for immediate rehabilitation of above-knee amputation," Int J Rehabil Res., 27(1):71-74, Mar. 1, 2004 [abstract only].
SBIR, "Pro-Active Dynamic Accommodating Socket" Solicitation Topic Code: OSD08-H18, 2 pages, Solicitation Year: 2008.
Smith, "Silver Linings for O&P Devices" The Academy Today, 1(4):A-8-A-9, Oct. 2005.
Spaeth, "Laser imaging and computer-aided design and computer-aided manufacture in prosthetics and orthotics," Phys Med Rehabil Clin N Am., 17(1):245-263, Feb. 28, 2006 [abstract only].
Turner, "Fit for Everyone," Yanko Design [online], <URL:http://www.yankodesign.com/2013/07/17/fit-for-everyone/>, 7 pages, Jul. 17, 2013.
Wilson et al., "Recent advances in above-knee prosthetics," Artif. Limbs., 12(2):1-27, Jan. 1, 1968.
Wilson Jr., "A material for direct forming of prosthetic sockets," Artif. Limbs., 14(1):53-56, Jan. 1, 1970.
Wu et al., "Technical note: CIR sand casting system for trans-tibial socket," Prosthet Orthot Int., 27(2):146-152, Aug. 2003.
Zhang, "Ethylene-vinyl acetate copolymer based on a continuous phase of duallpolycaprolactone blend of the porous material prepared," Yangzhou University, Materials Science, Master's Thesis, [USPTO translation of relevant portions of Zhang article], 131 pages, 2010.

* cited by examiner

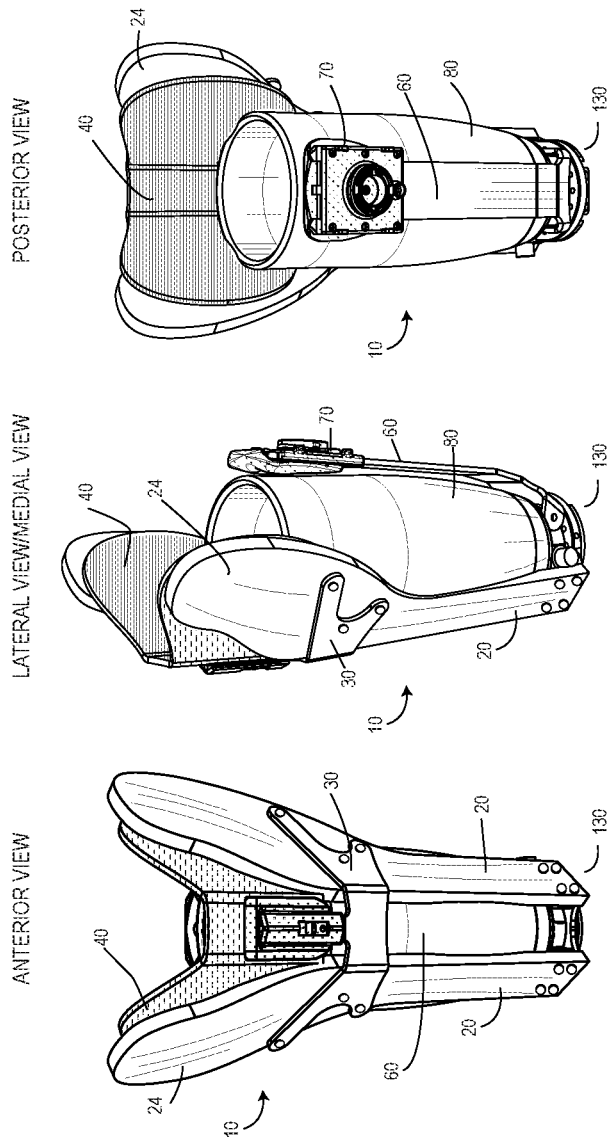

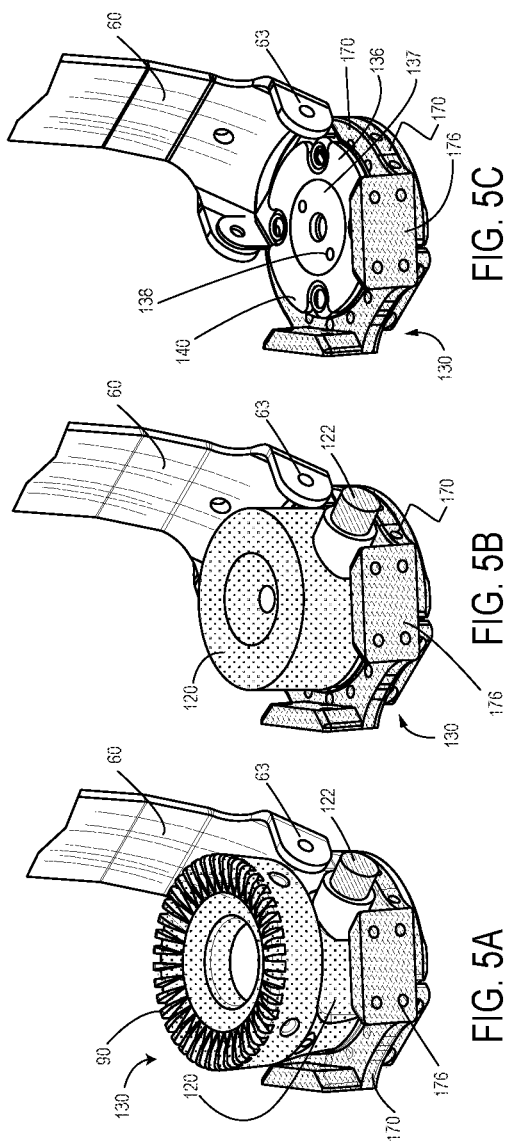

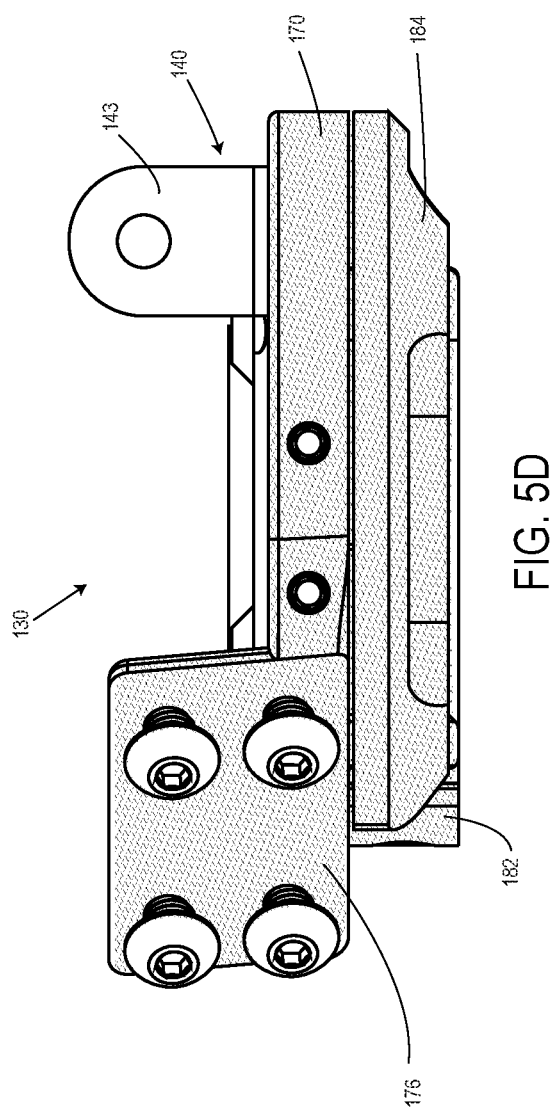

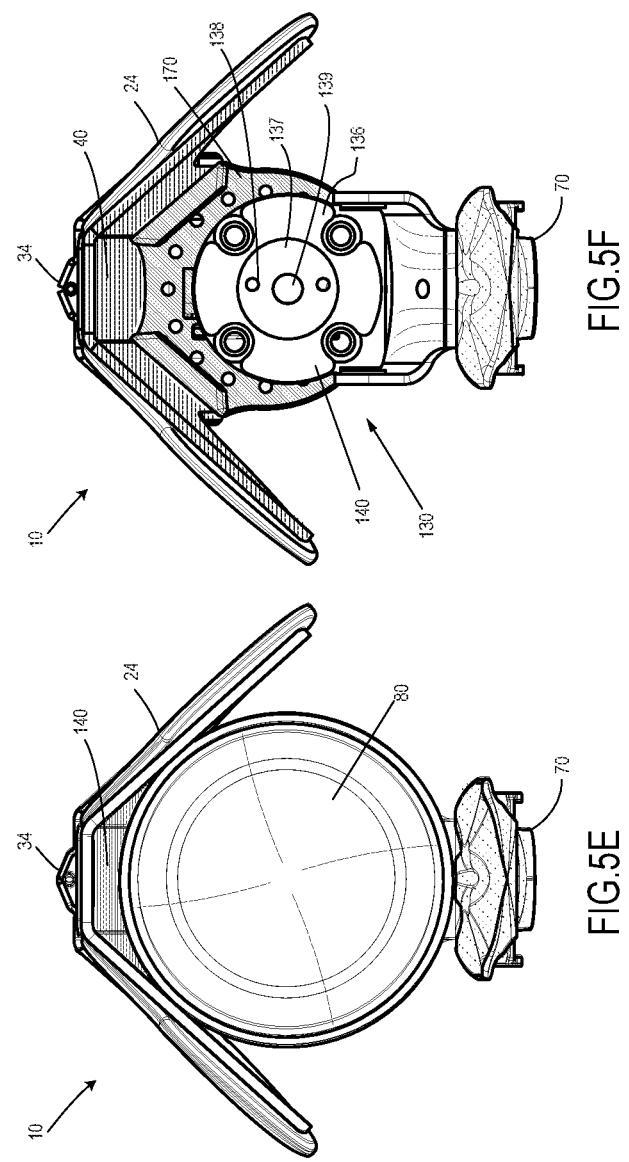

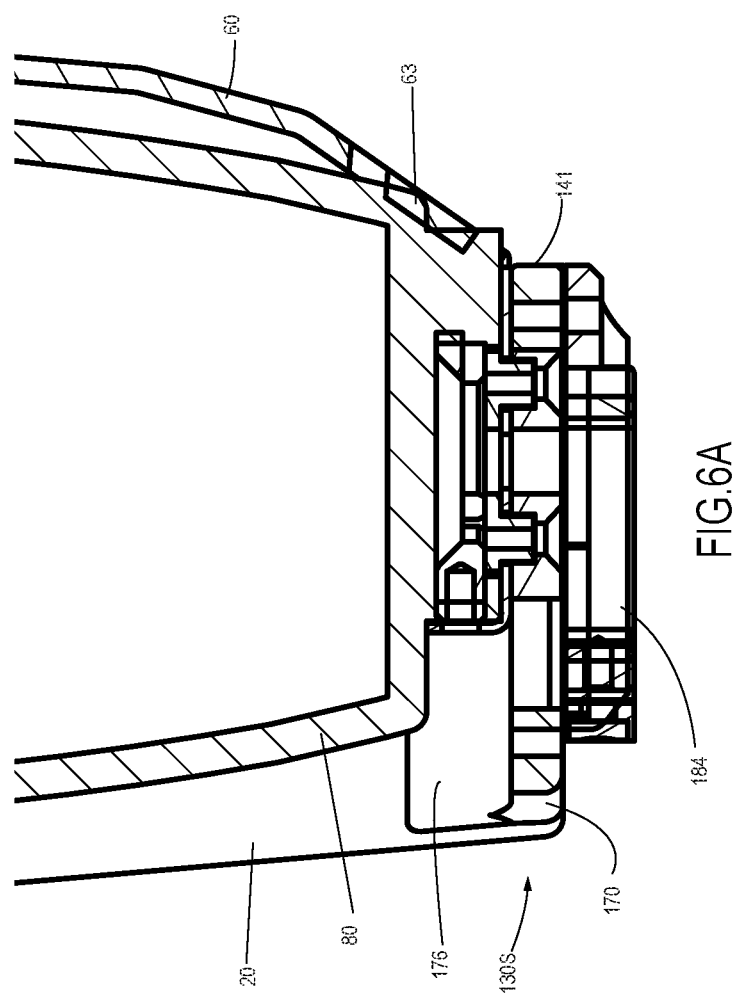

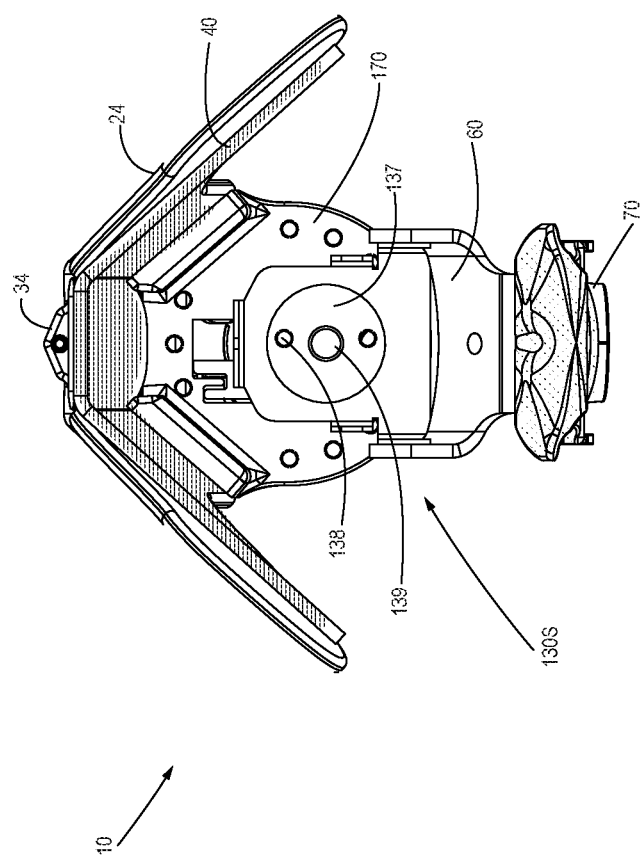

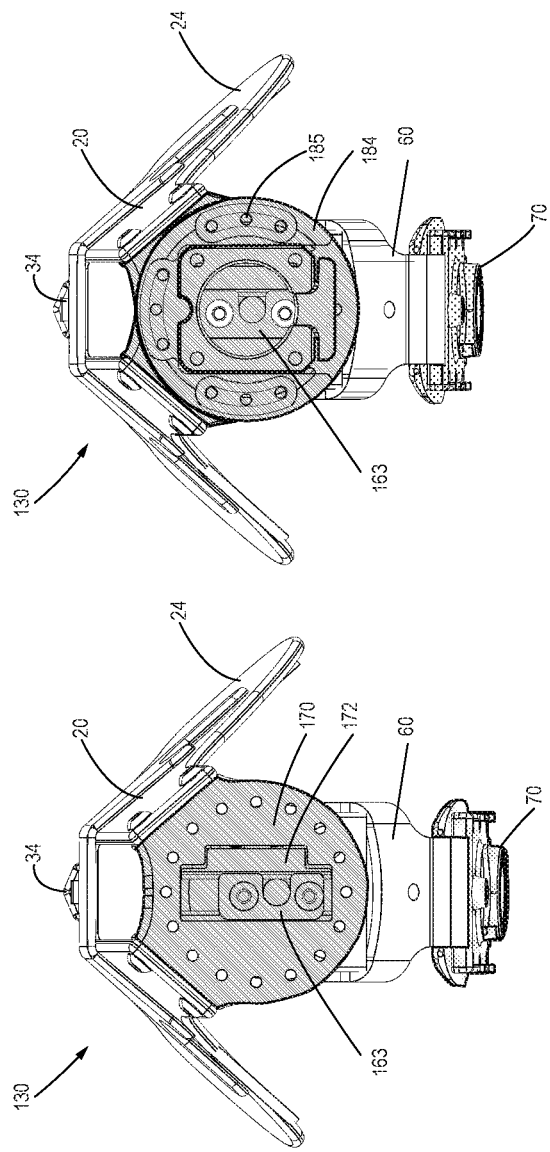

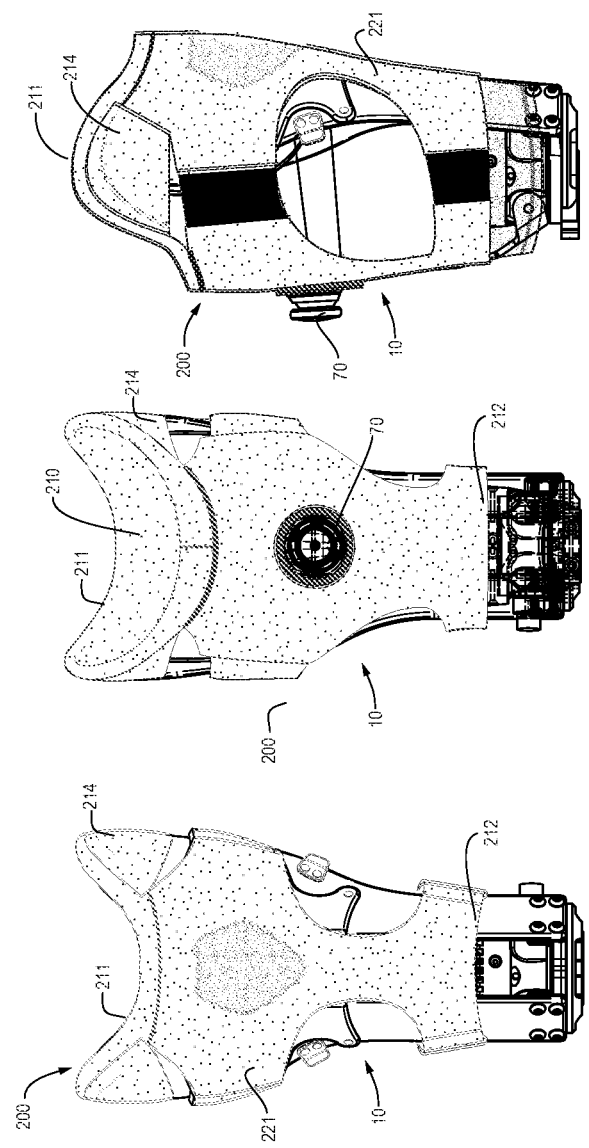

TRANSTIBIAL PROSTHETIC SOCKET WITH TEXTILE JACKET

CROSS-REFERENCE TO RELATED APPLICATIONS

This patent application claims priority to U.S. Provisional Patent Application Ser. No. 62/259,931 of Hurley et al., entitled "Prosthetic Socket with Positioning Sling," filed Nov. 25, 2015; 62/287,702 of Hurley et al., entitled "Prosthetic Socket with Positioning Sling," filed Jan. 27, 2016; and 62/305,477 of Hurley et al., entitled "Prosthetic Sockets with Textile-based Cover and Intra-frame Force Applicators", filed Mar. 8, 2016. The full disclosures of all of the above-referenced applications are hereby incorporated by reference herein.

INCORPORATION BY REFERENCE

All publications and patent applications identified in this specification are herein incorporated by reference to the same extent as if each such individual publication or patent application were specifically and individually indicated to be so incorporated by reference.

TECHNICAL FIELD

This disclosure relates to medical devices and methods. More specifically, the disclosure relates to a transtibial prosthetic socket frame and a prosthetic frame jacket.

BACKGROUND

Prosthetic limbs for the lower extremities typically include a residual limb socket, an alignment system, and distal prosthetic components to complete the limb. The prosthetic socket is the portion of the prosthesis designed to fit on the residual limb, grasp it securely, and provide the functional connection to the distal components. If the prosthetic socket does not fit properly, it will inevitably be uncomfortable for the patient, even to a level of intolerability. Even the most advanced prosthetic limb components distal to the socket will not serve the patient well, if the socket fits poorly. Ultimately, the prosthetic socket needs to enable the patient to efficiently translate her or his functional intention into functional actuality, by way of the prosthetic limb components distal to the prosthetic socket.

Aside from the universal issues of fit, comfort, and functionality, the amputee population is diverse in many ways, and there is thus a demand in the market for diversity in the types of prosthetic sockets. Diversity in the population of patients follows from conventional demographic variables, such as body weight, age, K-level, and individual levels of activity and personal preferences. It is also common for amputee patients to have more than one prosthetic socket, as well as more than one set of distal prosthetic components, which they use according to the specifics of activity in which they are engaged. The Infinite Socket™ system of LIM Innovations, Inc. (San Francisco, Calif.) is an example of a transfemoral (TF) prosthetic socket that is able to fit many patients, due to its modular assembly, its numerous adjustable features, and its use of thermoplastic fiber composite materials that permit a thermal reforming of components to optimize fit.

No matter how advanced the design, components, or materials, any prosthetic socket still involves a tradeoff between (a) versatility/adjustability and (b) increased complexity, weight, and bulk. A complement to a prosthetic socket with such options as possessed by the Infinite Socket™ system could thus be a socket with a narrower range of adjustable hardware options, but with an overall leaner profile that could be attractive to many patients, as, for example, those who engage in high performance activity.

Protecting the distal end of the residual limb from having to bear the load of the body weight of the patient is a particular challenge in the fitting of a transtibial prosthetic socket. The distal end of an amputated bone lacks the condyle of an intact bone, which, when intact, enables durable and functional load bearing. Thus, it is desirable for a prosthetic socket to spare the distal end of the residual limb from such load bearing by distributing the load elsewhere. In one approach, compression of the socket around the residual limb is helpful, in that it can distribute load away from the distal end of the residual limb and across a larger surface area of the residual limb through points of contact with the socket. In another approach, load can be distributed toward the most proximal region of the socket, where an appropriately contoured brim element can absorb load, transferring it away from the residual limb itself and onto the pelvis.

Still, protecting the distal end of the residual limb from having to bear the load of the body weight of the patient, even if done well, may not fully enable the functional optimization that might be desirably provided by a prosthetic socket. The residual limb is not a monolithic structure; the bones are not firmly locked within muscle like concrete, and the muscles themselves have a degree of movement independence from each other. Compression of the residual limb by a prosthetic socket may create a firmness of the limb as a whole, but it does not transform the residual limb into a monolithic structure. Further, excessive compression is not tolerated well for prolonged periods by patients, and it can bring a host of undesired effects. In addition to challenges associated with load distribution, the transtibial residual limb is missing its former distal portion, which normally acts to provide biomechanically intelligent leverage through that portion of the limb, and to stabilize the position of the upper portion of the limb as it connects to the body through the hip.

Despite the very significant advances made by the Infinite Socket™ system, additional improvements in prosthetic sockets are still being sought. It would be ideal, for example to have a prosthetic socket with improved ability to distribute forces placed on the residual limb as it is hosted within the socket in a biomechanically appropriate and normalizing manner. It would also be ideal to have a prosthetic socket designed for a transtibial residual limb. At least some of these objectives will be met by the embodiments described below.

SUMMARY

A transtibial prosthetic socket may include a frame and one or more additional socket features, such as interfacing features disposed between the frame and a hosted residual limb, and/or a fabric jacket arranged over internal and external aspects of the frame. A method of applying the prosthetic socket for supporting the transtibial residual limb of a patient is also described.

In one aspect of the present disclosure, a frame of a prosthetic socket for a transtibial residual limb of a patient may include a distal base assembly, a set of longitudinal struts (including two anterior struts and a posterior strut) supported by the distal base assembly, and a patellar bar arranged across the anterior struts. The distal base assembly may include a base plate, a carriage disposed proximal to the base plate, and a distal prosthetic component connection adapter disposed distal to the base plate. The carriage may support a prosthetic socket suspension arrangement, and the adapter may be configured for connection to a distal prosthetic component. Longitudinal struts may include two anterior struts (a medial anterior strut and a lateral anterior strut) and a single posterior strut. The set of struts and the distal base assembly, collectively, define a prosthetic socket cavity that defines a central longitudinal axis and a residual limb hosting volume. Embodiments of the distal prosthetic component connection adapter are (a) rotatable with respect to the base plate, and (b) moveable with respect to the base plate between a position aligned with the prosthetic socket's central longitudinal axis and a position offset from the socket's central longitudinal axis.

In some embodiments, the anterior struts and the posterior strut include a thermoplastic fiber composite material, the fiber of the composite material including a continuous fiber. In particular embodiments, the anterior struts and the posterior strut are formed entirely from a thermoplastic fiber composite material, and the fiber of the composite material is a continuous fiber. Further, in some particular embodiments, one or more of the anterior struts and the posterior strut are custom molded to conform to contours of an individual transtibial residual limb.

In some embodiments, the carriage and the base plate may be moveable with respect to each other along an anterior-posterior axis. This movability feature allows an adjustment of the residual limb hosting volume by way of adjusting the nominal circumference of a cross-sectional circle (as defined by the struts) and may be used to adjust the fit of the socket to the residual limb.

In some embodiments, the distal base assembly (in addition to the base plate, carriage and connector) may also include a through slot having an anterior-posterior alignment within the base plate and a sliding dovetail piece disposed therein. A locking nut may be disposed proximal to the carriage and a sliding dovetail piece may be disposed within the through slot in the base plate, the through slot having an anterior-posterior alignment within the base plate. One or more bolts that pass through the carriage, connecting the locking nut and the sliding dovetail piece to each other. In such embodiments, the carriage and the base plate are moveable with respect to each other when the one or more bolts are loose, and the carriage and the base plate are fixed in position relative to each other when the one or more bolts are tight.

Further to embodiments that include a through slot and a sliding dovetail piece, the distal base assembly may include a wall clamp disposed within the through slot that is configured to be pressable against the dovetail piece; when the wall clamp is pressed against the dovetail piece, the dovetail piece is thereby locked in place, within the through slot.

Distal base assembly configurations may vary according to the type of suspension arrangement provided by the prosthetic socket. In some embodiments, the suspension arrangement includes a flexible inner liner that is connected to the distal base assembly by way of a pin lock mechanism. In other embodiments, the suspension arrangement includes a roll on liner that is suspended on the residual limb by way of a suction mechanism.

Some embodiments of the distal base assembly prosthetic socket include a distal prosthetic component connector that includes a supporting clamp into which the distal prosthetic component connection adapter is seated, the connection adapter comprising a center. In some of these embodiments, the supporting clamp of the distal prosthetic component connector is rotatable with respect to the base plate, thereby enabling the rotatability of the connection adapter. In some of these embodiments, the supporting clamp has a crescent shape with an opening that faces in an anterior direction when the clamp is in a neutral, non-rotated position with respect to the distal base. In particular examples of these embodiments, the connecting adapter is slidable within the supporting clamp such that the center of the connection adapter can be adjustably offset from the central longitudinal axis of the prosthetic socket cavity. In some embodiments of the distal base assembly, the distal prosthetic component connector is rotatable with respect to the distal base plate and further configured to offset a center of the distal prosthetic component connecting adapter, wherein these abilities to rotate and to offset are translatable to a distal prosthetic component coupled to the prosthetic socket.

In some embodiments of the prosthetic socket frame, the posterior strut is connected to the distal base assembly by a hinged mechanism. In some of these embodiments, the proximal strut is supported by the distal base assembly by way of a carriage that is moveable with respect to the distal base plate. In particular embodiments, the proximal strut, by virtue of the hinged mechanism, is externally openable from an upright position, and wherein the hinge is freely positionable at a desired angle to provide an adjustment of the residual limb hosting volume Some embodiments of the prosthetic socket further include a tensioning mechanism configured to adjustably apply inwardly directed pressure on the set of struts. Embodiments of the tensioning mechanism include a tensioning anchor housing, a tensioning actuator mounted on the tensioning anchor housing, and at least one tensioning cable arranged to connect the tensioning anchor housing and tensioning cable guides mounted on the set of struts.

In embodiments of the tensioning mechanism, the tensioning anchor housing is mounted on the posterior strut at its proximal end, and the tensioning actuator is disposed on an external surface of the tensioning anchor housing. In some of these embodiments, the tensioning anchor housing is mounted on the posterior strut in a height adjustable manner. In some embodiments of the tensioning mechanism, the at least one tensioning cable is arranged to compress (a) a proximal aspect of each of the pair of anterior struts, as a unit, and (b) the posterior strut toward each other. And in some embodiments of the tensioning mechanism, the at least one tensioning cable is arranged to connect the tensioning anchor housing to each of the anterior struts.

Some embodiments of the prosthetic socket further include a tensioning mechanism configured to adjustably apply inwardly directed pressure on the set of struts by way of a circumferentially arranged tensioning path. Embodiments of the path include a tensioning cable connected to a tensioning anchor housing mounted on the posterior strut, two cable guides (wherein one of the cable guides is coupled to each of the two anterior struts, the tensioning cable looped through each of the strut-coupled cable guides), portions of each the two anterior struts; and a patellar bar arranged between the two anterior struts.

Some embodiments of the circumferentially arranged tensioning path summarized above further include a strap arranged across an external aspect of the anterior struts, the strap having two ends (each of the two ends terminating proximate a posterior edge of an anterior strut), a strap cable guide coupled to each end of the strap, wherein the tensioning cable is looped through each of strap-coupled cable guides.

Some embodiments of the circumferentially arranged tensioning path summarized above further include an intra-frame applicator having a proximal edge and distal edge, the force applicator coupled by a hinge on its proximal edge to an interior aspect of a proximal edge of the tensioning anchor housing, the distal edge of the force applicator being inwardly deflectable, wherein the circumferentially arranged tensioning path further includes a tensioning cable channel through the distal edge of the force applicator, the tensioning cable being threaded therethrough.

Some embodiments of the prosthetic socket further include an intra-frame force applicator disposed on an internal aspect of the posterior strut, applicator being configured to apply an inwardly directed pressure on the residual limb when the applicator is tensioned by the socket's tensioning mechanism, as summarized above. In some embodiments, the intra-frame force applicator is positioned at the proximal end of the posterior strut, and when tensioned, the intra-frame force applicator applies an anteriorly directed pressure on the popliteal region of the residual limb. In particular embodiments, anteriorly directed force applied by the intra-frame force applicator is separate from and in addition to any anteriorly directed force applied by the posterior strut itself.

In embodiments of the prosthetic socket frame, each anterior strut comprises a proximal clasping portion that extends posterior-ward and is contoured to conform to the residual limb. In some of these embodiments, the prosthetic socket frame further includes a patellar bar connecting the two anterior struts. In such embodiments that include the patellar bar connecting the two anterior struts, the patellar bar supports a proximally directed mounting post, the prosthetic socket further comprising a knee pressure distribution pad mounted on the mounting post, the knee pressure distribution pad disposed internal to the anterior struts. In some embodiments, the knee pressure distribution pad is height adjustable on the mounting post.

In some embodiments, the knee pressure distribution pad includes a thermoplastic fiber composition. And in particular embodiments, the knee pressure distribution pad is thermally shaped to conform to a patellar aspect of the residual limb.

Some embodiments of the prosthetic socket further include one or more air bladders positioned within the prosthetic socket frame, the air bladders being arranged and configured to interface between the frame and the residual limb of the patient. In some embodiments, one of the air bladders is positioned on an internal surface of a knee pressure distribution pad, the knee pressure distribution pad being supported by a patellar bar suspended between the two anterior struts. In some embodiments, one of the air bladders is positioned on the internal surface of a distal portion of the anterior struts.

Some embodiments of the prosthetic socket further include two or more air bladders positioned internal to the prosthetic socket frame, the air pressure within each of the two or more air bladders being controllable by inflation and deflation. In some of these embodiments the air pressure within each of the two or more air bladders is controllable independently of the other one or more air bladders.

In some embodiments of the prosthetic socket frame, (a) as a unit, a proximal portion of each of the anterior struts and a patellar bar supported by the anterior struts and (b) the posterior strut, collectively, can be compressed together by a tensioning mechanism. Such compression can manifest both as an anterior-posterior compression and as a lateral-medial compression.

Some embodiments of the prosthetic socket are arranged and configured so as to enable a controllable adjustment of the residual limb hosting volume. Accordingly, in some embodiments of prosthetic socket frame, the residual limb hosting volume of the prosthetic socket cavity is configured to be adjustable by way of an adjustment of a variable anterior-posterior position of the carriage with respect to the distal base plate. In such embodiments, the residual limb hosting volume of the prosthetic socket cavity can be maximized by moving the carriage to a posterior-most position with respect to the distal base plate and the volume can be minimized by moving the carriage to an anterior-most position with respect to the distal base plate.

In another aspect of adjustability of the residual limb hosting volume, in some embodiments of the prosthetic socket, the prosthetic socket cavity can adjusted to optimize fitting the residual limb by way of a thermal reforming adjustment of the contours of any of the anterior or posterior struts.

In yet another aspect of adjustability of the residual limb hosting volume, in some embodiments of the prosthetic socket, the prosthetic socket includes one or more tensioning cables. In such embodiments, a volume of the prosthetic socket cavity can be adjusted to optimize fitting the residual limb by way of an adjustment of the tension of tensioning cables.

Some embodiments of prosthetic socket further include a fabric jacket that includes a central tubular section configured to be positioned internal to the set of struts and an exterior section configured to be positioned external to the set of struts, the central tubular portion and the external sections joined at their respective proximal edges. In some of these embodiments, the fabric jacket includes a suspension pocket at two sites, the sites disposed at the joining of the central tubular and external sections, these sites configured to be arranged over the proximal portions of the two anterior struts. In some of these embodiments, the fabric jacket may further include insert pieces positioned within the suspension pockets; and in some of these embodiments, the insert pieces may include a thermoplastic composition. In particular embodiments of the fabric jacket, the exterior section of the fabric jacket comprises an anterior section and a posterior section, these sections being joined by an elastic fabric.

In another aspect of the present disclosure, a method of supporting a transtibial residual limb of a patient is described. The method may involve embracing the residual limb with a prosthetic socket and adjusting a fit of the prosthetic socket on the residual limb by (a) adjusting a residual limb hosting volume of the prosthetic socket cavity and/or (b) changing the shape of the prosthetic socket cavity. A transtibial prosthetic socket suitable for enabling embodiments of this method includes a set of struts (including two anterior struts and a posterior strut) and a distal base assembly that includes a base plate configured to support the set of struts. The set of struts and the distal base assembly collectively define a residual limb hosting cavity that defines a volume and a central longitudinal axis.

Some embodiments of the method involve use of a transtibial prosthetic socket having struts with a thermoplastic fiber material composition. In such embodiments, the method includes changing the shape of the prosthetic socket cavity by altering one or more contours of any one or more of the struts. Altering strut contours includes warming at least one of the struts or a portion thereof to a sufficient temperature and for a sufficient time that the strut becomes malleable; and reshaping the at least one malleable strut to include one or more desired contours such that the fit of the prosthetic socket on the transtibial residual limb is improved.

Various methods of adjusting the residual limb hosting volume of a transtibial prosthetic socket cavity in order to optimize fit, and accordingly to provide an optimal ability to support the residual limb are provided. Accordingly, in some embodiments, a method of supporting a transtibial residual limb by adjusting the residual limb hosting volume of the prosthetic socket cavity includes adjusting a distance at the distal base assembly between (a) the anterior struts, as a unit, and (b) the posterior strut. Adjusting this distance can be understood in terms of the various geometric consequences, including adjusting the diameter of a circle nominally defined by the struts at the distal base, consequently adjusting the cross-sectional area as nominally defined by that circle, and ultimately, adjusting the volume of the cavity as a whole.

In some embodiments of the provided transtibial prosthetic socket, the posterior strut is hinged at its connection to the distal base assembly. In the context of such embodiments, adjusting the residual limb hosting volume of the prosthetic socket cavity includes adjusting an angle of the posterior strut with respect to the distal base assembly. Adjusting the angle of the posterior strut has the geometric consequences of adjusting the cross-sectional area and the volume of the prosthetic socket cavity.

In some embodiments of the provided transtibial prosthetic socket, a circumferential tensioning system is anchored on the prosthetic socket frame. In the context of such socket embodiments, adjusting the residual limb hosting volume of the prosthetic socket cavity includes adjusting a level of tension in the circumferential tensioning mechanism. Adjusting the tension of a circumferential tensioning mechanism has the geometric consequences of (as summarized above) of adjusting the cross-sectional area and the volume of the prosthetic socket cavity In some embodiments of the provided transtibial prosthetic socket, the socket includes a circumferential tensioning anchor supported by the posterior strut, which is height adjustable on the strut. In the context of such socket embodiments, supporting the transtibial residual limb of a patient may include adjusting the height of the circumferential tensioning anchor with respect to the distal base assembly.

In some embodiments of the provided transtibial prosthetic socket, the socket includes a knee pressure distribution pad supported by the anterior struts that is height adjustable on the struts. In the context of such socket embodiments, supporting the transtibial residual limb of a patient may include adjusting the height of the knee distribution pad with respect to the distal base assembly.

In some embodiments of the provided transtibial prosthetic socket, the socket includes a knee pressure distribution pad that has a thermoplastic fiber composite composition. In the context of such socket embodiments, supporting the transtibial residual limb of a patient may include shaping the knee pressure distribution pad by way of warming the knee pressure distribution pad or a portion thereof to a sufficient temperature and for a sufficient time that the knee pressure distribution pad becomes malleable, and then shaping the knee pressure distribution pad to include one or more desired contours such that the fit of the prosthetic socket on the transtibial residual limb is improved.

In some embodiments of the transtibial prosthetic socket, the knee pressure distribution pad supports a proximal fluid bladder on its interior aspect. In the context of such particular socket embodiments, supporting the transtibial residual limb of a patient may include reshaping the knee pressure distribution pad, and in so doing, reshaping the proximal fluid bladder.

In some embodiments of the provided transtibial prosthetic socket, the socket includes one or more air bladders attached to an internal aspect of the prosthetic socket frame, and thus disposed within the prosthetic socket cavity. In the context of such socket embodiments, a method of supporting the transtibial residual limb of a patient may include adjusting the volume of residual limb hosting cavity within the boundaries defined by the set of struts and the distal base assembly, wherein adjusting the volume of the residual limb hosting cavity includes adjusting a level of air pressure in the bladder.

In some embodiments of the provided transtibial prosthetic socket, the socket includes at least two bladders within the prosthetic socket residual limb hosting cavity, a proximal bladder and distal bladder. In the context of such prosthetic socket embodiments, the method of supporting the residual transtibial limb of a patient may include adjusting the volume of residual limb hosting cavity within the boundaries defined by the set of struts and the distal base assembly, the volume adjusting including adjusting a level of air pressure in one or more of the at least two bladders, the level of air pressure in the each of the air bladders being independently adjustable.

In some embodiments of the provided transtibial prosthetic socket, the socket includes an inwardly deflectable intra-frame force applicator mounted on one of the struts of the set of struts, the intra-frame force applicator deflectable toward an interior of the prosthetic socket cavity. In the context of such socket embodiments, the method of supporting the transtibial residual limb of a patient may include adjusting a position of the residual limb within the cavity by tensioning the intra-frame force applicator. In particular embodiments of a transtibial prosthetic socket that have an inwardly deflectable intra-frame force applicator, the applicator is mounted the posterior strut, and tensioning the intra-frame force applicator adjusts the position of the residual limb toward an anterior aspect of the interior of the prosthetic socket cavity.

In some embodiments of the provided transtibial prosthetic socket, the distal base assembly includes a distal prosthetic component connection adapter configured to connect the prosthetic socket to a distal prosthetic component, wherein the connection adapter is configured to adjust an alignment of a central longitudinal axis of the distal prosthetic component with respect to the central longitudinal axis of the prosthetic socket. In the context of such embodiments, supporting the residual limb may include aligning the central longitudinal axis of the distal prosthetic component with respect to the central longitudinal axis of the prosthetic socket in a manner that is biomechanically appropriate for the patient.

Some embodiments of the method of aligning the distal prosthetic component with respect to the central longitudinal axis of the socket include coupling the distal prosthetic connection adapter of the distal base assembly to the distal prosthetic component.

Particular embodiments of the distal base assembly of the prosthetic socket further include a distal prosthetic component connector that comprises a supporting clamp into which the distal prosthetic component connection adapter is seated, and wherein the distal prosthetic socket connector is rotatable with respect to the distal base plate. In the context of such embodiments, aligning the distal prosthetic component with respect to the central longitudinal axis of the socket may include rotating the clamp with respect to the base plate.

In particular embodiments of the distal prosthetic component connection adapter are horizontally slidable with respect to the base plate proximal thereto. In the context of such embodiments, aligning the distal prosthetic component with respect to the central longitudinal axis of the socket may include sliding the slidable adapter to vary an offset position of the prosthetic component connector relative to the central longitudinal axis of the prosthetic socket.

Particular embodiments of prosthetic socket for a hosted transtibial residual limb that includes a distal base unit having a distal prosthetic component connector configured for connection to a distal prosthetic component; and a set of longitudinal struts supported by the distal base unit, the set of struts comprising two anterior struts, a medial anterior strut and a lateral anterior strut, and at least one posterior strut, wherein the distal base unit and the set of longitudinal struts, collectively define a prosthetic socket cavity comprising a central longitudinal axis and a residual limb hosting volume. In typical embodiments, the anterior struts are supported directly by the distal base unit; in some embodiments, the at least one posterior strut may be supported by distal base unit by way of support from the anterior struts.

In some embodiments of the prosthetic socket, the struts within the set of struts comprise a thermoplastic fiber composite material, and each anterior strut has a proximal clasping portion that extends posterior-ward and is contoured by way of thermal reshaping to conform to the residual limb.

Some embodiments of the prosthetic socket include a tensioning mechanism that is configured to adjustably apply inwardly directed pressure on the set of struts by way of a circumferentially arranged tensioning path, the path comprising a tensioning cable arranged across a gap between posterior edges of the two anterior struts. In particular examples of these embodiments, the tensioning cable is arranged across a gap between posterior edges of the two anterior struts in two traverses.

Some embodiments of the prosthetic socket include a tensioning mechanism that is configured to adjustably apply inwardly directed pressure on the set of struts by way of a circumferentially arranged tensioning path, the path comprising a strap attached to an exterior aspect of the two anterior struts.

Some embodiments of the prosthetic socket include a tensioning mechanism that is configured to adjustably apply inwardly directed pressure on the set of struts by way of a circumferentially arranged tensioning path, wherein the tensioning path, when tensioned, is sufficiently strong to effect a compression of the set of struts toward each other, thereby reducing a volume of the prosthetic socket cavity.

Some embodiments of the prosthetic socket include a knee pressure distribution pad mounted supported by the anterior struts, the knee pressure distribution pad disposed internal to a proximal aspect of the anterior struts and arranged to span across a gap between the anterior struts.

Such a method includes embracing the residual limb with a prosthetic socket and adjusting a fit of the prosthetic socket on the residual limb by any one or more of (a) adjusting a residual limb hosting volume of the prosthetic socket cavity or (b) changing the shape of the prosthetic socket cavity. A transtibial prosthetic socket suitable for enabling embodiments of this method includes a set of struts (including two anterior struts and one or more posterior struts) and a distal base assembly that includes a distal base unit to support the set of struts, wherein the set of struts and the distal base collectively define a residual limb hosting cavity comprising a volume and a central longitudinal axis.

Some embodiments of the method are particularly enabled by the properties of a transtibial prosthetic socket having struts with a thermoplastic fiber material composition. In such embodiments, the method includes changing the shape of the prosthetic socket cavity by altering one or more contours of any one or more of the struts. Altering strut contours includes warming at least one of the struts or a portion thereof to a sufficient temperature and for a sufficient time that the strut becomes malleable; and reshaping the at least one malleable strut to include one or more desired contours such that the fit of the prosthetic socket on the transtibial residual limb is improved.

In some embodiments, a circumferential tensioning system is anchored on the prosthetic socket frame. In the context of such socket embodiments, adjusting the residual limb hosting volume of the prosthetic socket cavity includes adjusting a level of tension in the circumferential tensioning mechanism. Adjusting the tension of a circumferential tensioning mechanism has the geometric consequences of (as summarized above) of adjusting the cross-sectional area and the volume of the prosthetic socket cavity.

These and other aspects and embodiments will be described in further detail in the following description, in relation to the attached drawing figures.

BRIEF DESCRIPTION OF DRAWINGS

FIGS. 2A-2C are anterior perspective, lateral perspective and posterior perspective views, respectively, of the transtibial prosthetic socket frame of FIGS. 1A-1C;

FIG. 5A is a top perspective view of a distal base assembly of transtibial prosthetic socket configured for a pin lock suspension arrangement, showing a proximally facing funnel within the distal base assembly that is configured to support a suspension arrangement, according to one embodiment;

FIG. 5B is a top perspective view of the distal base assembly of FIG. 5A, showing a pin lock body within the distal base assembly;

FIG. 5C is a top perspective view of the distal base assembly of FIGS. 5A and 5B, showing a dual nut and a spacer within the distal base assembly;

FIG. 5D is a side view of the distal base assembly of FIGS. 5A-5C;

FIG. 5E is a top view of the distal base assembly of FIGS. 5A-5D, with a prosthetic socket liner in place;

FIG. 5F is a top view of the distal base assembly of FIGS. 5A-5E, with the prosthetic socket liner removed;

FIG. 6A is a cross-sectional view of a distal base assembly of a transtibial prosthetic socket configured for a suction based suspension arrangement, according to one embodiment;

FIG. 6B is a top view of the distal base assembly of FIG. 6A;

FIG. 7A is a bottom view of a distal base assembly of a transtibial prosthetic socket, without a supportive clamp and a distal prosthetic component connection adapter, thereby exposing the distal base plate, according to one embodiment;

FIG. 7B is a bottom view of the distal base assembly of FIG. 7A, showing a supportive clamp and a distal prosthetic component connection adapter, according to one embodiment;

FIGS. 12A-12C are anterior, posterior and lateral views, respectively, of a transtibial prosthetic socket frame with a prosthetic socket jacket disposed over it, according to one embodiment;

DETAILED DESCRIPTION

Figure 1C:
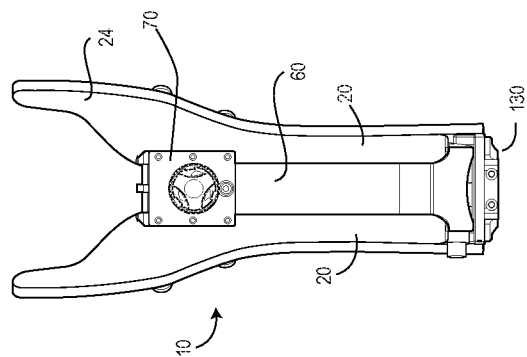
FIGS. 1A-1C are anterior, lateral and posterior views, respectively, of a transtibial prosthetic socket frame, according to one embodiment.
Figure 1B:
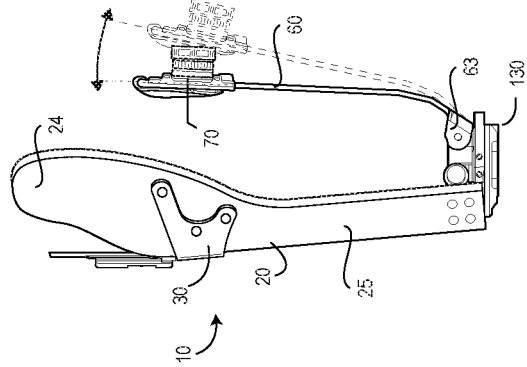
Figure 1A:
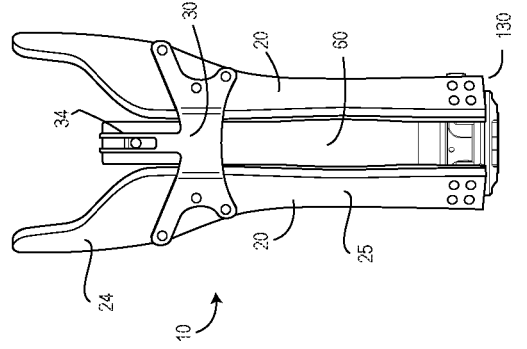

A modular transtibial (below knee) prosthetic socket (FIGS. 1A-14) is described herein. FIGS. 1A-2C focus on side and perspective views of a transtibial prosthetic socket frame 10, according to one embodiment. FIGS. 1A-1C show, respectively an anterior side view, a lateral side view, and a posterior view of an embodiment of a transtibial prosthetic socket frame 10. FIG. 1B shows, in particular, a range of motion of the posterior strut, as provided by a hinged connection 63 to the distal base assembly 130. FIGS. 2A-2C show, respectively, an anterior top perspective view, a lateral top perspective view, and a posterior top perspective view an embodiment of the transtibial prosthetic socket frame 10. The perspective views provided by FIGS. 2B-2C show a flexible inner liner 80 in place, within the prosthetic socket cavity. Flexible inner liner 80 is not shown in FIGS. 1A-1C, and is not visible in FIG. 2A. Details of structure, fabrication, and composition of a flexible inner liner are provided in U.S. patent application Ser. No. 14/663,360

(Publication US 2015/0265434) of Hurley et al., entitled "Modular Prosthetic Socket," filed Mar. 19, 2015, which is hereby incorporated into the present application by reference.

In this application, the reference number 10 refers to a transtibial prosthetic socket or to a portion thereof, such as a frame of the transtibial prosthetic socket or a portion of the frame. Any reference to a socket, a prosthetic socket, or a prosthetic socket frame refer particularly to a transtibial prosthetic socket. Further, prosthetic socket frame 10 may include some variation in componentry, particularly in the distal base assembly (130 or 130S), such variation being present to adapt to different suspension systems, such as a pin lock suspension system or a suction-based suspension system, respectively, as will be described further below.

In one embodiment, a prosthetic socket frame 10 includes a pair of longitudinally arranged anterior struts 20 and a longitudinally arranged posterior strut 60, which may be collectively referred to as a "set of struts." Prosthetic socket frame 10 further includes a patellar bar 30 coupled to the anterior struts 20, and a distal base assembly 130 that supports the set of struts (anterior struts 20 and posterior strut 60). The set of struts and distal base assembly 130 collectively define a prosthetic socket interior cavity that is configured to host and support a patient's transtibial residual limb. The volume and shape of this cavity are subject to a number of adjustments that collectively provide a highly customized fit to an individual residual limb, as described further below.

Each of the anterior struts 20 includes a proximal portion 24 and distal portion 25, the boundary between proximal and distal portions approximately defined by the site where patellar bar 30 attaches to each of the two anterior struts 20. As described further below, the proximal portion 24 of anterior struts 20 is broadened to extend proximally and contoured to fit the residual limb by a custom molding method.

A mounting post 34 extends proximally from the central section of patellar bar 30 to support a knee pressure distribution pad 40 (FIGS. 2A-2C). The height of knee pressure distribution pad on mounting post 34 is adjustable. Details of this arrangement are shown in greater detail in FIGS. 8A-8E, as described further below.

As noted above, posterior strut 60 may be connected to distal base assembly 130 by way of hinged connection 63. The hinged movement afforded by hinge 63 is shown in FIG. 1B, where posterior strut 60 is shown both in a substantially vertical position and in an outwardly deflected position by ghosted lines, the range of motion being indicated by an arrow. This hinged feature is shown in greater detail in FIGS. 5A-5C. The ability to open and close posterior strut 60 in such a manner is useful in donning and doffing prosthetic socket 10. Further, inasmuch as the angle of connection to distal base assembly 130 can be fixed by tensioning mechanisms (described further below), the variable angular position of posterior strut 60 provides an ability to vary the volume defined by the prosthetic socket cavity, and thereby provide an individually customized fit on a patient. In a fully assembled socket, the relative angle of posterior strut 60 from vertical is stabilized by tensioning mechanisms to be described further in detail elsewhere. The ability of posterior strut 60 to be fixed at a variable angle is one way, among others, to adjust the fit of prosthetic frame 10 on a patient's residual limb. Aspects of fit of prosthetic socket frame 10 that may be effected by features of posterior strut 60 include (1) hinged connection to distal base assembly 130, (2) a thermally reformable attribute of the strut 60 by virtue of its thermoplastic composition, and (3) a particular feature of distal base assembly 130, described elsewhere, that enables an adjustment of the distance between anterior struts 20 (as a unit) and posterior strut 60 at their sites of connection to the distal base assembly.

A tensioning anchor housing 70 may be mounted on the proximal end of posterior strut 60 in some embodiments, as shown in greater detail in FIGS. 9A-9F and 11A, 11D-11E, and as described further below. Tensioning anchor 70 serves as a central feature of a circumferential tensioning system around the set of prosthetic socket struts, which represents one of multiple features that allow for the volume and shape of the prosthetic socket cavity to be custom fitted for individual patients.

Figure 8B:
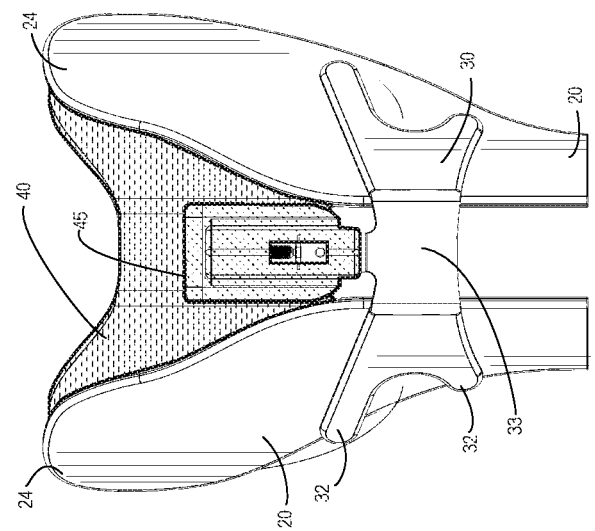
FIG. 8B is an anterior view of the proximal portion of FIG. 8A, showing a patellar bar extending between two anterior struts, the patellar bar supporting a knee pressure distribution pad on a support post.
Figure 8A:
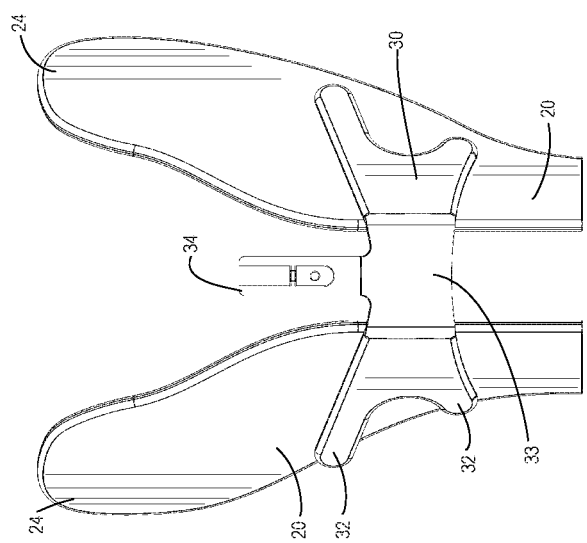
FIG. 8A is an anterior view of a proximal portion of a transtibial prosthetic socket frame, showing a patellar bar extending between two anterior struts, the patellar bar supporting a knee pressure distribution pad support post, according to one embodiment.

As shown in FIGS. 2A-2C, in some embodiments, a knee pressure distribution pad 40 may be supported by patellar bar 30, facing internally, into the prosthetic socket cavity, to engage the patellar tendon and the condyle portions of the knee. More particularly (as shown in FIGS. 8A-8B) knee pressure distribution pad 40 includes a mounting piece 45 that is configured to engage a mounting fork 34 that projects proximally from a central bridging section 33 of patellar bar 30. The arrangement by which female mounting piece 45 and mounting fork 34 engage is height adjustable, thereby allowing knee pressure distribution pad 40 to be height adjustable with respect to a floor represented by distal base assembly 130.

In typical embodiments, anterior struts 20 are broadly flat, but contoured to custom fit the particular features of a patient's residual limb (FIGS. 1A-2C). Anterior struts 20, as well as posterior strut 60, may be formed of a thermoplastic fiber composite composition, and in some embodiments the fiber of the composite material may be in the form of a continuous fiber. Thus, custom contouring may be performed on the struts 20, 60 by way of thermal reforming. This reformable attribute of anterior struts 20 allow them to be custom molded to fit the contours and dimensions of a patient's residual limb, and particularly to fit the contours and dimensions of the patient's knee. Patellar bar 30 (FIGS. 1A-2B, 8A-8B) may engage each anterior strut 20 at a substantially central point on the strut 20. A proximal portion 24 of each anterior strut 20 may include a flared and contoured aspect that is configured to wrap posteriorly around the condyle portion of a residual limb.

In a typical fabrication process, the stock commercial material from which struts 20, 60 are cut is flat. By virtue of their thermoplastic fiber composite composition, struts may be thermally reformed or molded to assume contours that complement the contours of a patient's residual limb in a customized manner. Thermal reforming may occur by way of a direct molding of struts against a mold of the patient's limb, by direct molding of the struts against the patient's limb, albeit protected by layer of thermal insulation, or by way of molding within a reconfigurable surface apparatus and by methods, such as those described in U.S. Patent Application Publication No. 2015/0352775 of Geschlider, et al., entitled "Method and Apparatus for Transferring a Digital Profile of a Residual Limb to a Prosthetic Socket Strut, filed Jun. 4, 2015, which is incorporated into the present application by this reference. Details of the thermoplastic fiber composition and methods of forming prosthetic socket struts are described in US Patent Application Publication No. US 2014/0277584 of Hurley et al., entitled "Modular prosthetic sockets and methods for making and using same", as filed on Mar. 14, 2014, which is also incorporated into the present application by this reference.

In some embodiments of prosthetic socket frame 10, a tensioning anchor housing 70 is mounted on the proximal end of posterior strut 60 (refer ahead to FIGS. 1B-1C, 3, 4, 9B-9F, 11A, 11C-11E). Tensioning anchor housing 70 supports a tensioning actuator 72 on an exterior surface 71, the tensioning actuator enabled to control the tension of one or more tensioning cables 74, whose actions are described in detail elsewhere.

Tensioning anchor 70 may further support an intra-frame force applicator 75 on an interior aspect of the tensioning anchor. Intra-frame force applicator 75 may take the form of a deflectable flap that is coupled at its proximal edge to a proximal edge of tensioning anchor 70, but unattached at its distal end, and thus inwardly deflectable. Inward deflection occurs by the action of tensioning cable 74, as described in further detail elsewhere. When deflected inward, intra-frame force applicator 75 presses inwardly or anteriorly against the popliteal region of residual limb 1.

Referring ahead to FIGS. 5A-5N and 6A-6C, some embodiments of prosthetic socket frame 10, a distal base assembly 130 includes a base plate 170, a carriage piece (140 or 141) configured to support a suspension mechanism is disposed proximal to base, and distal component connector 180 that is disposed distal to base plate 170; the distal component connector includes a distal prosthetic component connection adapter 182 slidably disposed within a supportive clamp 18, some embodiments of which are crescent shaped.

Figure 5I:
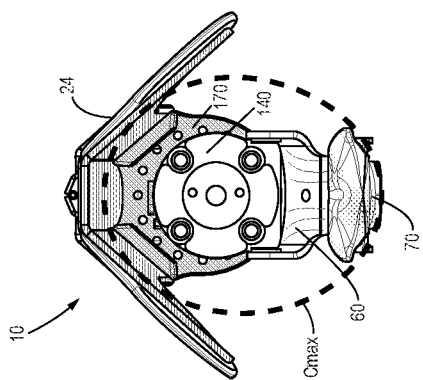
FIG. 5I is a top view of the distal base assembly of FIGS. 5A-5H, with the carriage disposed in its most anterior position, such position creating a maximum socket circumference as defined by the prosthetic socket struts.

Two variations of a carriage piece (140, 141) will be described that vary according to the type of suspension mechanism that is being used to suspend prosthetic socket from 10 from the residual limb of a patient. One suspension variation makes use of a pin lock suspension mechanism that is supported by a carriage embodiment 140 (FIGS. 5A-5N); a second suspension variation makes use of a suction or vacuum suspension mechanism that is supported by carriage embodiment 141 (FIGS. 6A-6C). The differences between carriage 140 and 141 are minor, and are described elsewhere. Within this patent application, a pin lock suspension version of distal base assembly 130 (with carriage piece 140) will generally be depicted and described. In describing and depicting features of a suction version of distal base assembly 130, (with carriage piece 141) such particular differences from the pin lock suspension version are specifically noted.

Base plate 170 embodiments include a through slot 171 that hosts a slidable dovetail piece 174 that can be locked in place by the action of a wall clamp 172 (refer ahead to FIGS. 5K-5N). Through slot 171 is disposed in an anterior-posterior orientation within the base plate. Dovetail piece 174 is connected by bolts to carriage (140 or 141, depending on the suspension arrangement) such that movement of dovetail piece 174 within through slot 171 drives movement of the carriage along an anterior-posterior axis with respect to base plate 170. Base plate 170 further includes flanges 143 that support the attachment of anterior struts 20. Posterior strut 60 is not directly supported by distal base plate 170, but rather by carriage (140 or 141) (which is supported by the distal base plate) via flanges 143.

Figure 5H:
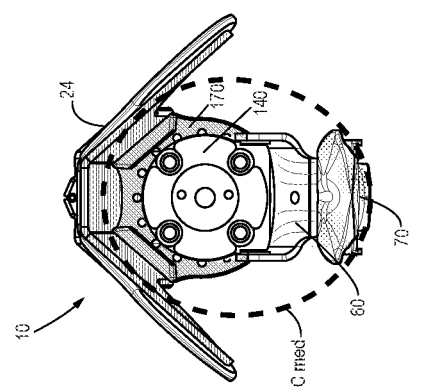
FIG. 5H is a top view of the distal base assembly of FIGS. 5A-5G, with the carriage disposed in a central position, such position creating a medium scale socket circumference as defined by the prosthetic socket struts.
Figure 5G:
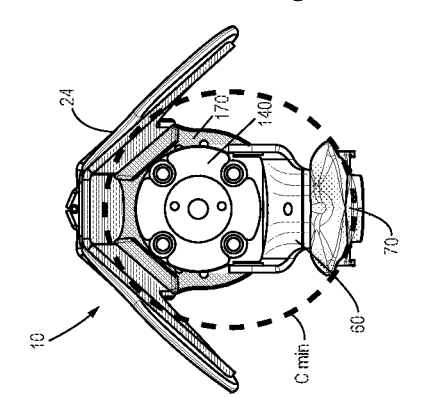
FIG. 5G is a top view of the distal base assembly of FIGS. 5A-5F, with a carriage disposed in its most anterior position, such position creating a minimal socket circumference as defined by the prosthetic socket struts.
Figure 5J:
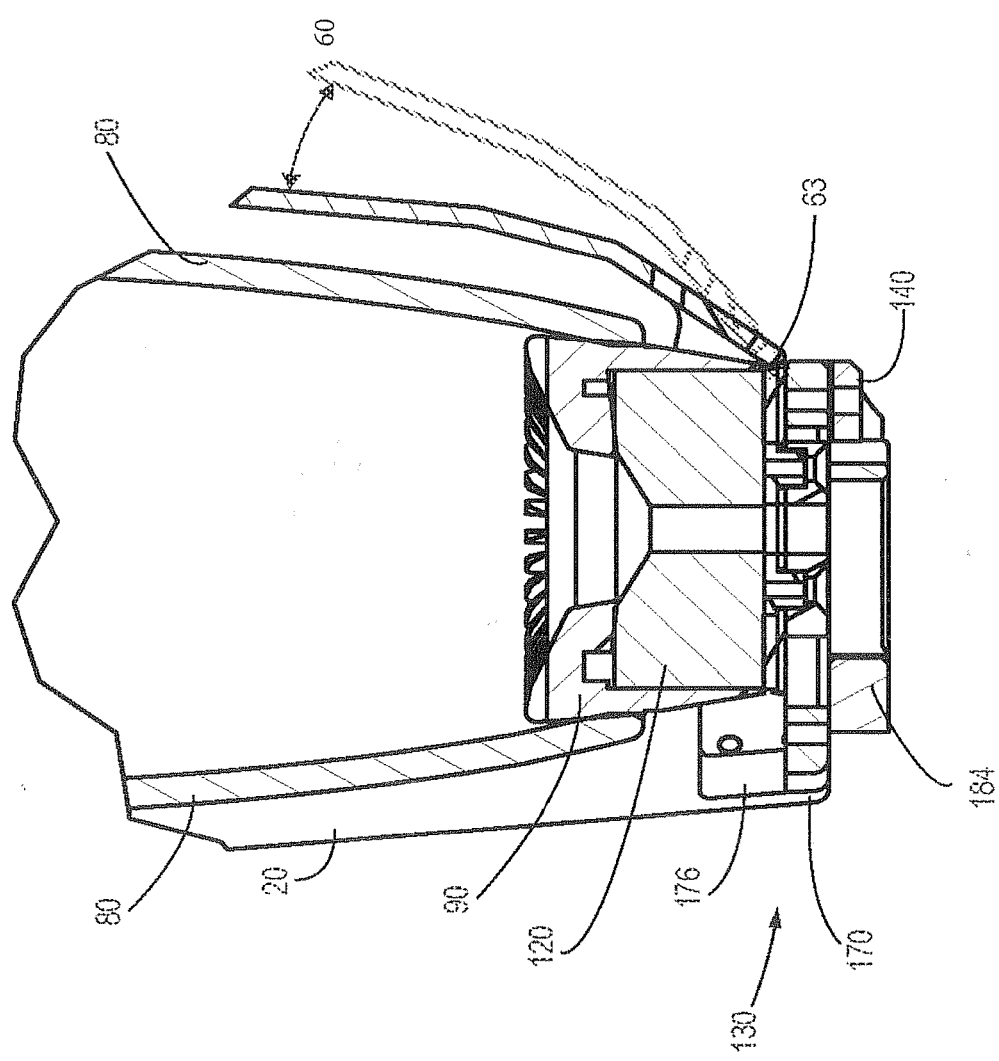
FIG. 5J is a cross-sectional view of the distal base assembly of FIGS. 5A-5I.
Figure 5K:
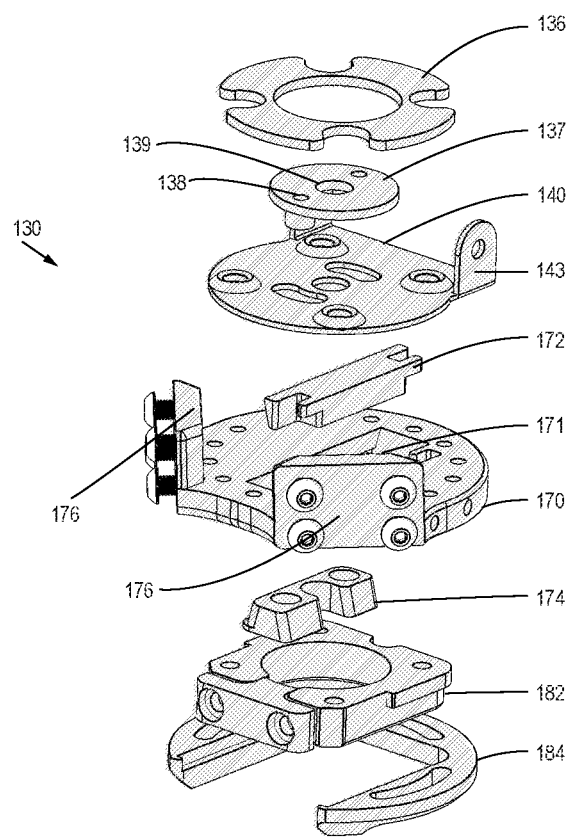
FIG. 5K is an exploded, top perspective view of the distal base assembly of FIGS. 5A-5J.
Figure 5L:
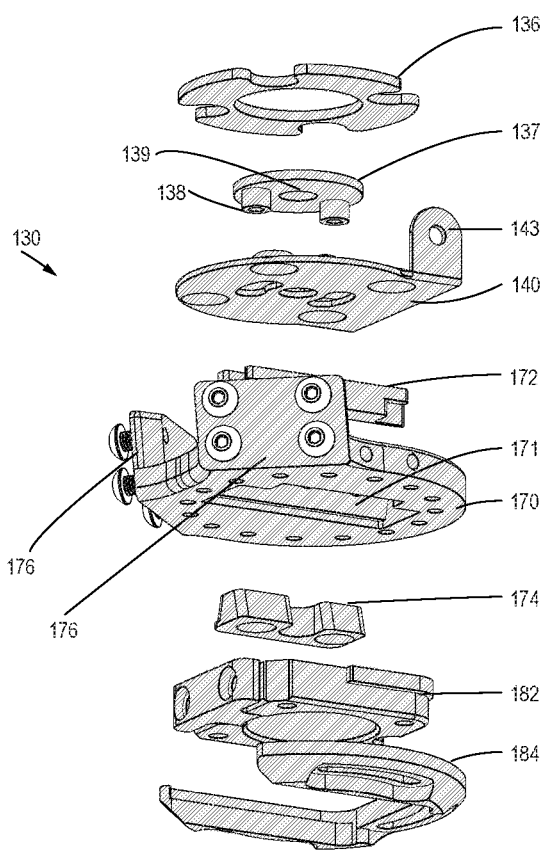
FIG. 5L is an exploded, bottom perspective view of the distal base assembly of FIGS. 5A-5K.
Figure 5M:
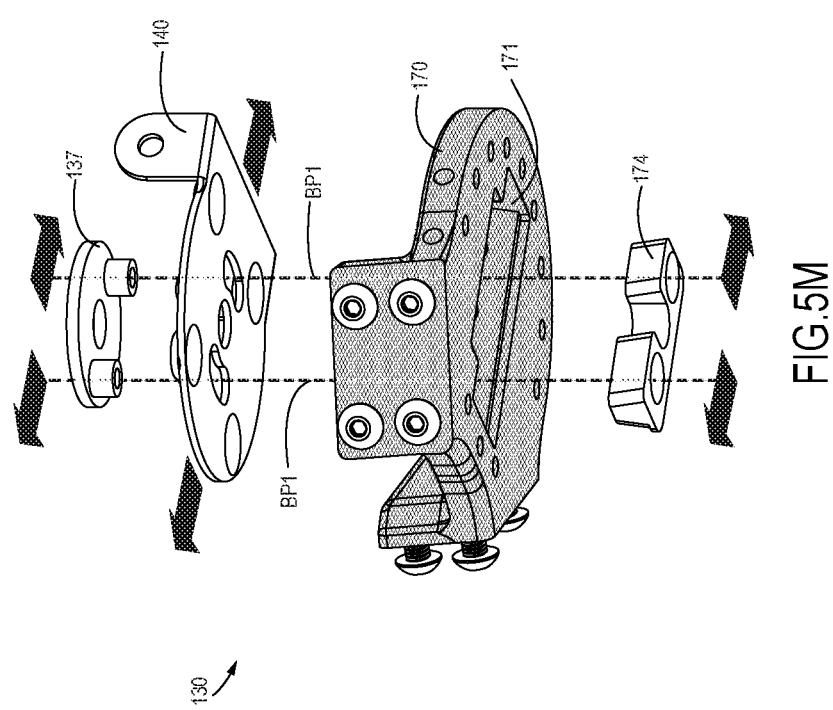
FIG. 5M is an exploded, bottom perspective view of a portion of the components depicted in FIG. 5L, with a focus on selected proximal components and their relationships.
Figure 5N:
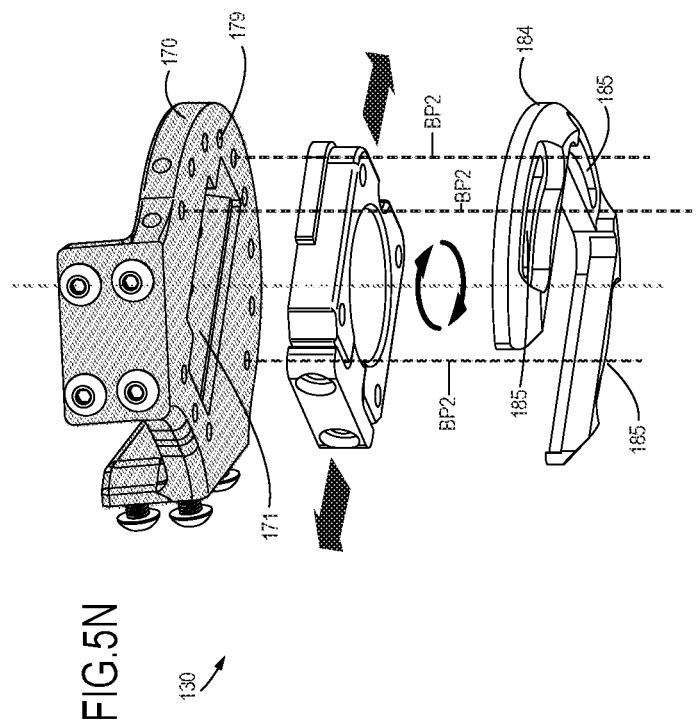
FIG. 5N is an exploded, bottom perspective view of a portion of the components depicted in FIG. 5L, with a focus on selected distal components and their relationships.
Figure 6C:
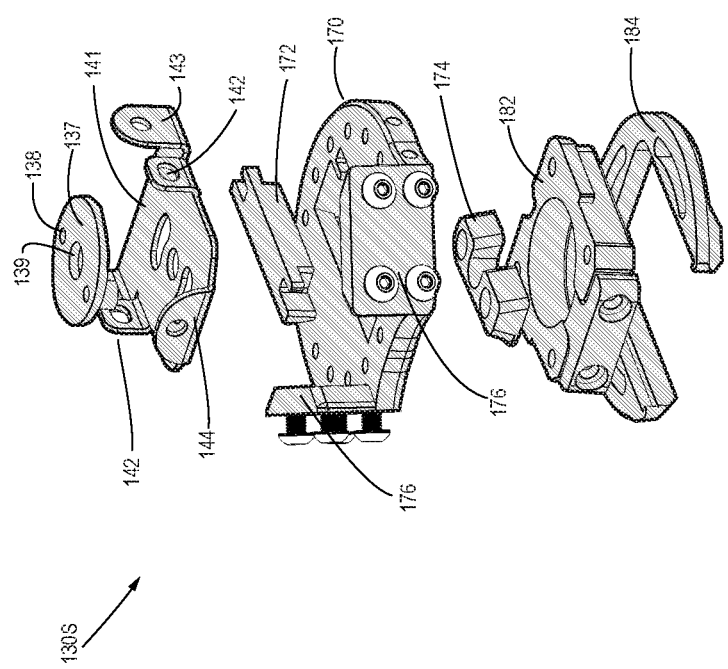
FIG. 6C is an exploded, top perspective view of the distal base assembly of FIGS. 6A and 6B.

In some embodiments, a distal base assembly 130 includes a supportive clamp 184, typically crescent shaped, disposed distal to distal base plate 170, the supportive clamp being rotatable with respect to the distal base plate see FIGS. 5K, 5L, 5N). Supportive clamp 184 hosts a distal prosthetic component connection adapter 182, that can mate with a conventional 4-hole adapter or with an M36 threaded adapter that can accept male or female pyramids for coupling to distal prosthetic components.

Many components within transtibial prosthetic socket frame 10 may be modular in character. Modularity refers generally to an arrangement in which a device is assembled from a collection of components that vary in size or shape, but yet, regardless of that variation, the components remain compatible such that they can be assembled into a complete device. Component compatibility is facilitated by retaining a fundamentally consistent configuration, and by retaining commonality regarding sites of connectability to other components and an ability to assemble with other components into a complete device. By virtue of the different sized and shaped components, a fully assembled device also may assume a variety of sizes and shapes. A facility that assembles a modular device typically maintains inventories of the modular components, the inventories having an array of like components that vary in size or shape. In some embodiments, inventoried components can be packaged as kits that include all the components necessary to assemble a complete device. By these various approaches, a modular device, such as a transtibial prosthetic socket, assembled from inventories of components, can be customized to fit transtibial residual limbs of a variety of sizes and shapes.

Modular components of a transtibial prosthetic socket may include, by way of non-limiting examples, any of anterior struts 20, posterior strut 60, patellar bar 30, and distal base assembly 130. Distal base assembly 130 is assembled from components that may have a modular character, such as carriage 140, and base plate 170. Middle goods, such as knee pressure distribution pad 40, proximal bladder 51, and distal bladder 55 may all be provided in a variety of modular shapes and sizes. Transtibial prosthetic socket jacket 200 also may be modular in character, by virtue of being assembled from sized versions of central tubular section 210, anterior exterior portion 221, and posterior exterior portion 231.

Figure 3:
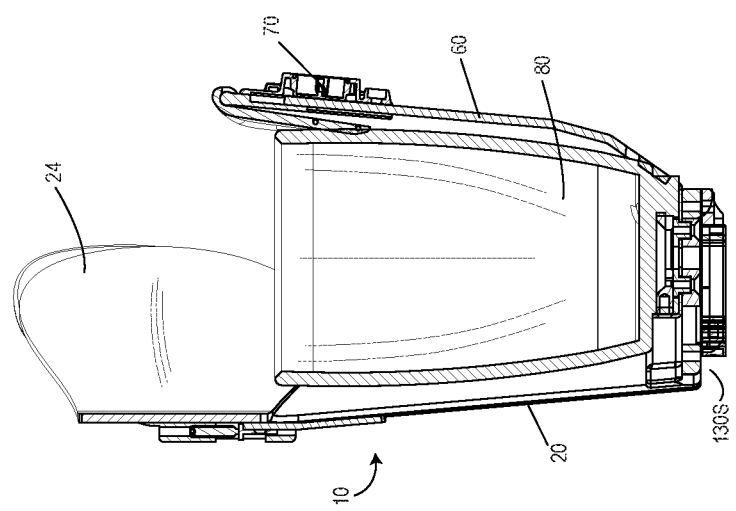
FIG. 3 is a longitudinal cross-sectional view of a transtibial prosthetic socket frame with a pin lock based suspension arrangement, according to one embodiment.
Figure 4:
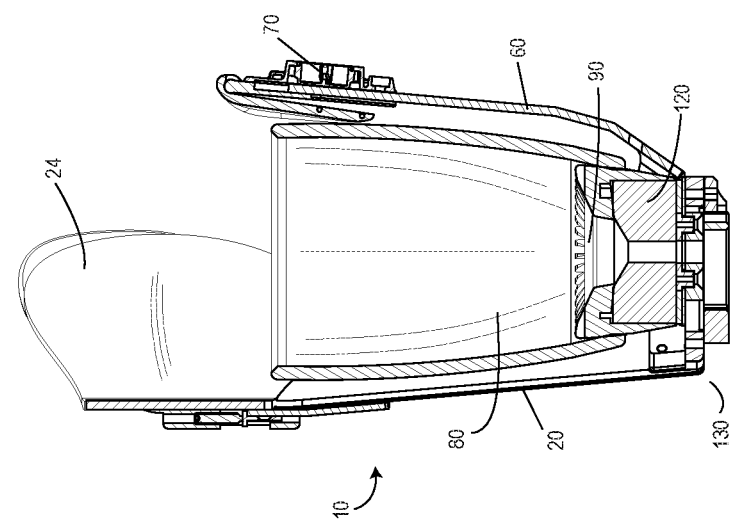
FIG. 4 is a longitudinal cross-sectional view of a transtibial prosthetic socket frame with a suction based suspension arrangement, according to one embodiment.

Referring now to FIGS. 3 and 4, two general types of embodiments of a transtibial prosthetic socket frame are disclosed herein. FIG. 3 shows a longitudinal cross-sectional view of a transtibial prosthetic socket frame 10, in one embodiment, which is configured with a pin lock based suspension arrangement. FIG. 4 shows a longitudinal cross-sectional view of a transtibial prosthetic socket frame 10, in an alternative embodiment, which is configured for suction based suspension arrangement. As can be seen, these two variations, depending on the suspension arrangement, are similar. Anterior struts 20 and posterior strut 60 connect respectively to a distal base assembly 130 (FIG. 3) or distal base assembly 130S (FIG. 4). These views of distal base assemblies 130 and 130S or too small to show much detail, but distal funnel 90 and cylindrical pin lock 120 are prominent in distal base assembly 130.

More detailed views of distal base assembly 130 are provided in FIGS. 5A-5L. More detailed views of distal base assembly 130S are provided in FIGS. 6A-6D. Componentry and the dynamics of the distal aspect of distal base assemblies 130 and 130S are identical, and are shown in FIGS. 7A-7E.

Referring now to FIGS. 5A-7E, distal base assembly 130 will now be described in further detail. In typical embodiments of prosthetic socket frame 10, a distal base assembly 130 includes a base plate 170, a carriage piece (140 or 141) configured to support a suspension mechanism, and distal component connection pieces disposed distal to base plate 170.

Embodiments of transtibial prosthetic socket frame 10 may be configured to accommodate two types of suspension arrangements, whereby the socket is suspended from a residual limb. In one suspension arrangement, prosthetic socket frame 10 (FIGS. 5A-5L) makes use of a pin lock suspension mechanism that is supported by a carriage embodiment 140; in a second suspension arrangement, prosthetic socket frame 10 (FIGS. 6A-6D) makes use of a suction or vacuum suspension mechanism that is supported by carriage embodiment 141.

Prior to stepping through FIGS. 5A-5L in detail (below), a brief overview of components and their relationship is provided. The exploded views of FIGS. 5K-5L may provide the best overall views of distal base assembly 130.

Thus, referring ahead to FIGS. 5K-5L, base plate 170 includes flanges 143 that support the attachment of anterior struts 20. Posterior strut 60 is not directly supported by distal base plate 170, but rather by carriage (140 or 141) (which is supported by the distal base plate) via flanges 143. Base plate 170 may further include a through slot 171 that hosts a slidable dovetail piece 174 that can be locked in place by the action of a wall clamp 172. Through slot 171 is disposed in an anterior-posterior orientation within base plate 170. Dovetail piece 174 is connected by bolts to carriage (140 or 141, depending on the suspension arrangement) such that movement of dovetail piece 174 within through slot 171 drives movement of the carriage along an anterior-posterior axis with respect to base plate 170. Such anterior-posterior movement of carriage 140 (or 141) occurs with respect to base plate 170. Inasmuch as anterior struts 20 are attached directly to base plate 170 and posterior strut 60 is attached to carriage 140 (or 141), movement of the carriage with respect to the base plate manifests as movement between the anterior struts (as a unit) and the posterior strut. Inasmuch as the anterior struts and the posterior strut nominally define the circumference of the prosthetic socket cavity, movement of the carriage with respect to the base plate constitutes a circumferential sizing option operable to adjust a fit of the socket to a hosted residual limb.

Returning now to FIGS. 5A-5C, these views show top perspective views of an embodiment (configured for pin lock-based suspension) of distal base assembly 130, with increasing levels of revealing disassembly. FIG. 5A shows a top perspective view of a distal base assembly of transtibial prosthetic socket configured for a pin lock suspension arrangement, showing, in particular, a proximally facing funnel 90 within the distal base assembly that is configured to support a suspension arrangement. Funnel 90 is configured to engage the distal end of a locking socket liner, which is described in detail in U.S. patent application Ser. No. 15/157,894 of Hurley et al., entitled "Prosthetic Liner Garment", filed May 8, 2016, which is incorporated into the present application by this reference.

FIG. 5B shows a top perspective view of a distal base assembly of a transtibial prosthetic socket with the funnel removed, thereby revealing cylindrical pin lock 120, operable by way of release button 122. A suitable cylindrical pin lock is provided by Fillauer LLC (Chattanooga, Tenn.). FIG. 5C shows a top perspective view of a distal base assembly of a transtibial prosthetic socket with cylindrical pin lock 120 and posterior strut 60 removed, thereby revealing the proximal surface of carriage 140. Disposed on the proximal surface of carriage 140 are a spacer piece 136 and a dual locking nut 137, which includes bolt holes 138. Bolt holes 138 host bolts that connect to dovetail piece 174 slidably disposed within through slot 171 of base plate 170 (bolts are not seen in this view).

FIG. 5D shows a lateral side view of distal base assembly 130 of a transtibial prosthetic socket configured for a pin lock suspension arrangement. This view is oriented with the anterior face on the left and the posterior face on the right. The most prominent visible aspect of carriage 140 is a posterior strut flange 143, an anchoring feature for hinged attachment to the distal end of posterior strut 60 (not shown). Prominently visible on the anterior aspect of base plate 170 is an anterior strut pedestal 176. Prominently visible distal to base plate 170 is supportive clamp 184, which slidably hosts distal prosthetic component connection adapter 182, edges of which are visible below and to the left of supportive clamp 184.

FIGS. 5E-5I show various top views of an embodiment of transtibial prosthetic socket 10, that is configured for pin lock based suspension; all figures are oriented such that the anterior aspect of the socket is at the top, and the posterior aspect of the socket is at the bottom of the figure. Accordingly, top views of twin anterior struts 20, particularly the broadened and contoured proximal portions 24 thereof are shown at the top of each figure, and the tensioning anchor housing 70 (disposed atop posterior strut 60) is shown at the bottom of each figure. Knee pressure distribution pad is visible against the interior aspect of proximal portions 24 of anterior the anterior struts.

FIG. 5E shows an embodiment of a flexible inner liner 80 in place, which obscures a view of underlying carriage 140. In FIG. 5F, flexible inner liner 80 has been removed and posterior strut 60 has been flexed outward to provide more exposure of the distal base portion of the prosthetic socket cavity. Dual nut piece 137 and spacer 136 are shown; they obscure a view of carriage 140 which is disposed immediately below. An anterior portion of base plate 170 is visible around the anterior periphery of spacer piece 136. Refer ahead to exploded perspective views of FIGS. 5K-5L to understand relationships among these various components.

FIGS. 5G-5I all show a top view of socket with an embodiment of distal funnel 90 in place, thus obscuring more distal components of distal base assembly 130. These figures focus on the spatial consequences, per a top view, of anterior-posterior movement of carriage 140 with respect to base plate 170, neither of which is visible in this top view.

As shown variously in FIGS. 5A-5D, anterior struts 20 attach directly to base plate 170 by way of pedestal 176 and posterior strut 60 attaches to carriage 140 by way of flange 143. Since carriage 140 is movable in an anterior-posterior alignment with respect to base plate 170, the distance between the two anterior struts 20 and posterior strut 60 can be varied. As that distance is varied, so too is the nominal circumference of a circle defined by these three struts. That variable circumference corresponds to a variable volume defined by the prosthetic socket cavity, which provides a variable by which prosthetic socket 20 can be custom fitted to an individual patient.

FIG. 5G shows a top view of an embodiment of a distal base assembly when the carriage disposed in its most anterior position, such position creating a minimal socket circumference Cmin as defined by the prosthetic socket struts. FIG. 5H shows a top view of a distal base assembly when the carriage is disposed in a central position, such position creating a medium scale socket circumference Cmed as defined by the prosthetic socket struts. FIG. 5I shows a top view of a distal base assembly when the carriage disposed in its most anterior position, such position creating a maximal socket circumference Cmax as defined by the prosthetic socket struts. The underlying mechanics of this anterior-posterior movement is shown in FIG. 5M.

FIG. 5J shows a cross-sectional view of a distal base assembly 130 of a transtibial prosthetic socket 10, as configured for a pin lock suspension arrangement, in one embodiment. FIG. 5J provides a particularly clear view of the how distal funnel 90 is positioned over and around cylindrical pin lock 120. Distal funnel 90 is described in detail in U.S. patent application Ser. No. 15/157,894 of Hurley et al., entitled "Prosthetic Liner Garment", as filed on May 18, 2016, which is incorporated into this present application. Further visible in cross-section are base plate 170, a portion of strut pedestal 176, an anterior strut 20, carriage 140, posterior strut 60 and its hinged distal attachment 63 to carriage 140, and supportive crescent clamp 184.

FIGS. 5K and 5L show vertically exploded top perspective (FIG. 5K) and bottom perspective (FIG. 5L) views of a distal base assembly 130 of a transtibial prosthetic socket configured for a pin lock suspension arrangement, in one embodiment. From top to bottom, the exploded components include spacer 136, dual locking nut 137, carriage 140, wall clamp 172, base plate 170, dovetail piece 174, and distal prosthetic connector 180, which includes distal prosthetic component connection adapter 182 and supportive clamp 184.

When components are arranged into a distal base assembly 130, spacer 136 and locking nut 137 are coplanar, dual locking nut 137 residing within the spacer 136 and stabilized thereby. A series of bolt holes align that allow connection by dual locking nut-dovetail bolts (not shown) to connect dual locking nut 137 to dovetail piece 174. These include bolt holes 138 within dual locking nut 137, bolt holes 145 within carriage 140, and bolt holes 175 within dovetail piece 174. The dual locking nut-dovetail bolts are part of a locking mechanism that stabilizes the relative anterior-posterior relationship between base plate 170 and carriage 140. When the dual locking nut-dovetail bolts are loose, carriage 140 can move with respect to base plate 170; when these bolts are tightened, carriage 140 and base plate 170 are fixed in position. This relationship is described further below. The function of the ability of carriage 140 to move with respect to base plate 170 relates to the distance between anterior struts 20 (as a unit), which are attached to base plate 170, and posterior strut 60, which is attached to carriage 140. The consequence of this variation in distance between anterior struts 20 (as a unit) and posterior strut 60 is depicted in FIGS. 5G-5I, as described above.

Base plate 170 has a through slot 171 aligned in an anterior-posterior orientation. Only a small portion of the slot is visible FIG. 5K; it is more visible in the bottom view of FIG. 5L. The longitudinal walls of slot 171 are canted, the lower opening of the slot being wider than the upper opening. Wall clamp 172 and dovetail piece 174 both reside within the slot, side by side. The lateral walls of dovetail piece 174 are also canted, the piece being wider at its base than at its top. When bolts (not shown) within the dual nut-dovetail piece aligned bolt holes (dual nut bolt holes 138, carriage bolt holes 145, and dovetail bolt holes 175) are tightened, dovetail piece 174 is secured within though slot 171, but remains free to slide therein. As described elsewhere, a wall clamp 172, which co-resides with dovetail piece 174 within through slot 171, can be pressed against the dovetail piece with set screws to lock it in place.

FIGS. 5M-5N each depict selected components of distal base assembly 130 for the purpose of explaining their relationships and how they enable movements that allow for custom fitting of transtibial prosthetic socket 10 to individual patients. FIGS. 5M and 5N are arranged in a manner similar to that depicted in FIG. 5K.

FIG. 5M shows a vertically exploded bottom perspective view of a portion of distal base assembly 130 of a transtibial prosthetic socket configured for a pin lock suspension arrangement, showing, in particular (from top to bottom), dual locking nut 137, carriage 140, base plate 170, and dovetail piece 174, which resides within through slot 171 of the base plate 170. Two bolt paths BP1 originate (at the top) from dual locking nut, pass through bolt holes in carriage 140, through slot 171 of base plate 170, and terminate within bolt holes of dovetail piece 174. These bolt paths BP1 maintain dual locking nut 137, carriage 140 and dovetail piece 174 in a fixed relationship.

When bolts (not shown) in bolt paths BP1 are loose, dual locking nut 137, carriage 140 and dovetail piece 174 are free to move within the bounds of longitudinal through slot 171 of base plate 170, and thus move, as a unit, with respect to base plate 170; this anterior-posterior movement is shown by arrows. When bolts in bolt paths BP1 are tightened, dual locking nut 137 and carriage 140 are pulled down toward base plate 170, and dovetail piece 174 is drawn up into through slot 171, thereby securing all of these components in a fixed relationship. These mechanical relationships underlie the anterior-posterior movement of anterior struts 20 (as a unit) with respect to posterior strut 20 (as seen in FIGS. 5G-5I), and represent one of several approaches to adjusting of the volume and shape of the cavity of transtibial prosthetic socket 10 so as to create an individualized custom fit to a residual limb, as provided by transtibial prosthetic socket 10.

FIG. 5N shows a vertically exploded bottom perspective view of a portion of distal base assembly 130, showing, in particular, base plate 170, distal prosthetic component connection adapter 182, and support clamp 184. Although shown above support clamp 184 in this view, note that when assembled, distal prosthetic component connection adapter 182 resides within the rectangular receptacle of support clamp 184. A plurality of bolt holes 179 can be seen arranged around the periphery of base plate 170. Two of these are used as originating sites for two exemplary bolt paths BP2, which extend from base plate 170 through curved through slots 185 of crescent shaped support clamp 184. These bolt paths BP2 are external to the external boundaries of distal prosthetic component connection adapter 182.

When bolts (not shown) in bolt paths BP2 are loose, (1) distal prosthetic component connection adapter 182 is free to slide in an anterior-posterior alignment within the rectangular receptacle of crescent shaped support clamp 184 and (2) crescent shaped support clamp is free to rotate (within the arc boundaries of the curved through slots 185) with respect to base plate 170. When bolts in bolt paths BP2 are tightened, these three components (base plate, support clamp, and distal prosthetic component connection adapter) are secured into a fixed relationship. These mechanical relationship underlie the various offset and rotational movement of the distal prosthetic component adapter with respect to the base plate, as seen in the bottom views of FIGS. 7B-7E. These particular movements represent one of several approaches to adjusting of the volume and shape of the cavity of transtibial prosthetic socket 10, as provided herein so as to create an individualized custom fit of the transtibial prosthetic socket to a residual limb.

FIGS. 6A-6D show aspects of a distal base assembly 130S that is particularly configured to accommodate a suction-based suspension system for transtibial prosthetic socket frame 10. The differences in components and configuration of a suction-based suspension arrangement versus a pin lock-based suspension arrangement (as shown in FIGS.

5A-5L) are relatively minor; and are the focus of this descriptive section. FIG. 6A shows a cross-sectional view of a distal base assembly of a transtibial prosthetic socket configured for a suction based suspension arrangement, FIG. 6B shows a top view, and FIG. 6C shows a vertically exploded top perspective view.

The cross-sectional view (FIG. 6A) of distal base assembly 130S shows base plate 170, a portion of strut pedestal 176, an anterior strut 20, carriage 141, posterior strut 60 and its hinged distal attachment 63 to carriage 141, and supportive crescent clamp 184.

The top view (FIG. 6B) of distal base assembly 130S is shown with its anterior aspect at the top and the posterior aspect at the bottom. A flexible inner liner is not shown. The main distal base assembly components visible in this view are base plate 170, and dual locking nut 137 with bolt holes 138 and central hole 139. Anterior to the distal base assembly are anterior struts (only distal portion 24 is visible), knee distribution pad 40 disposed internal to distal portion of the struts, and mounting post 34 that supports knee distribution pad 40. Posterior to distal base assembly, an internal aspect of posterior strut 60 and tensioning anchor 70 can be seen.

FIG. 6C shows an exploded top view of a distal base assembly 130S of a transtibial prosthetic socket configured for a suction based suspension arrangement, in one embodiment. From top to bottom, the exploded components include dual locking nut 137, carriage 141, wall clamp 172, base plate 170, dovetail piece 174, and distal prosthetic connector 180, which includes distal prosthetic component connection adapter 182, and supportive clamp 184. Comparing to FIG. 5K, which shows an analogous view of components for distal base assembly 130 configured for a pin lock suspension arrangement, it can be seen that this distal base assembly 130S (configured as a suction suspension embodiment) lacks spacer piece 136, and that carriage 141 has a different configuration than that of carriage 140. Features unique to carriage 141 (vs. carriage 140, see FIG. 5L) are side flanges 142 and anterior flange 144, both of which are described further below in terms of their relation to anchor piece 82 (FIG. 6D).

Figure 6D:
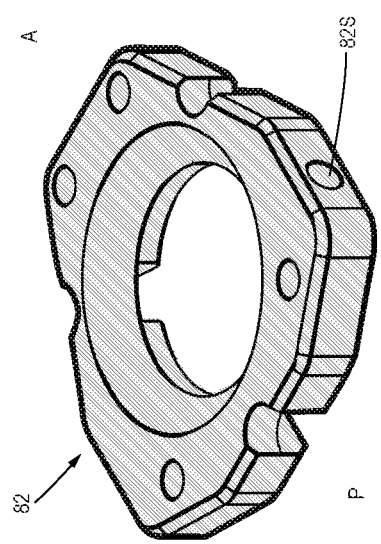
FIG. 6D is a perspective view of an isolated flexible inner liner anchor piece, which is embedded within the flexible inner liner, in some embodiments of the distal base assembly of FIGS. 6A-6C.

FIG. 6D shows perspective view of an embodiment of an isolated flexible inner liner triangular anchor piece 82, which is embedded within the floor of flexible inner liner 80 (as seen in FIG. 4). Anchor piece 82 is oriented in this view with the anterior aspect A in the upper right and the posterior aspect P in the lower left, a screw hole 82S is seen on the lower right side, an identical hole is on the opposite side, and another similarly configured hole is on the anterior side (not shown). Anchor piece 82, from its embedded poster position, engages carriage 130S (FIG. 6C) as follows: screw holes 82S align with side flanges 142 of the carriage and the unseen anterior screw hole aligns with anterior flange 144 of the carriage. When screws are applied through the flanges of carriage 130S and into the aligned screw holes of anchor piece 82, the carriage and flexible inner liner are securely connected, thus providing a critical suspension engagement whereby the prosthetic socket is suspended from the residual limb.

The distal components of distal base assembly 130 (configured for pin lock suspension) and distal base assembly 130S (configured for suction based suspension) are the same, thus bottom views, as shown in FIGS. 7A-7E apply to both assemblies, even as views are identified as distal base assembly 130.

Figure 7C:
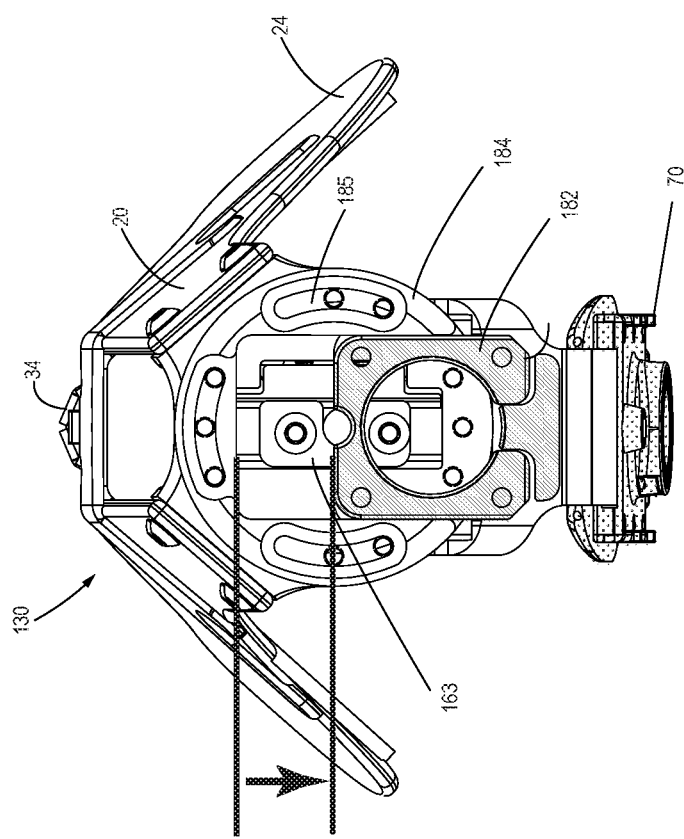
FIG. 7C is a bottom view of the distal base assembly of FIGS. 7A and 7B, showing a supportive clamp and a distal prosthetic component connection adapter that has been slidingly positioned offset from center.

FIGS. 7A-7E show various bottom views of an embodiment of distal base assembly 130 of transtibial prosthetic socket 10, including distal prosthetic connector 180, which includes distal prosthetic component connection adapter 182 and supportive clamp 184. FIG. 7A shows a bottom view of a distal base assembly 130 absent distal prosthetic component connection adapter 182 and supportive clamp 184, thereby exposing the base plate 170. This perspective affords a view of dovetail piece 163 and wall clamp 172, both residing within through slot 171 of base plate 170. Also provided here, and in FIGS. 7B-7E are bottom views of anterior struts 20 (attached proximally to base plate 170) and posterior strut 60 (attached proximally to carriage 140).

FIG. 7B shows a bottom view of distal base assembly 130 of transtibial prosthetic socket 10 with a supportive clamp 184 and a distal prosthetic component connection adapter 182 in place, thereby substantially obscuring the immediately proximal base plate 170. In this embodiment, supportive clamp 184 is crescent shaped, with an opening that faces in the posterior direction. Supportive claim 184 also has curved through slots 185 through which bolts may pass that originate from their proximal end through a circular series of bolt holes in base plate 170. This relationship is shown in further detail in FIG. 5N.

Distal prosthetic component connection adapter 182 is held within a rectangular receptacle of the crescent shaped supportive clamp 184, and can slide in the rectangular receptacle in an anterior-posterior alignment, as shown. The anterior-posterior alignment is being shown in this view, however supportive clamp 184 is rotatable with respect to the base plate 170, as shown in FIGS. 7D and 7E, as described below.

Figure 7D:
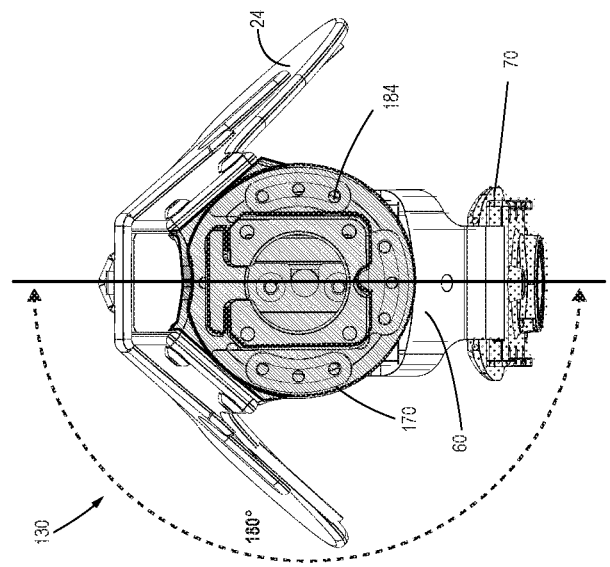
FIG. 7D is a bottom view of the distal base assembly of FIGS. 7A-7C, showing a supportive clamp and a distal prosthetic component connection adapter, the supportive clamp being rotated 45 degrees from neutral.
Figure 7E:
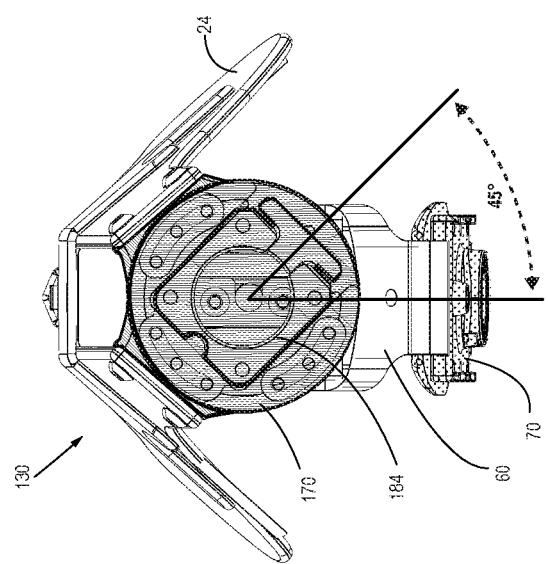
FIG. 7E is a bottom view of the distal base assembly of FIGS. 7A-7D, showing a supportive clamp and a distal prosthetic component connection adapter, the supportive clamp being rotated 180 degrees from neutral.

FIGS. 7C-7E each relate to aspects of movement of components in the distal portion of distal base assembly 130 that relate to alignment of prosthetic distal prosthetic components (i.e., prosthetic components that are connected distally to the distal base assembly, such as a pylon or foot) with respect to the main body of the prosthetic socket. Some of the underlying mechanical features that enable these movements are detailed in FIG. 5N.

FIG. 7C shows a bottom view of distal base assembly 130 of a transtibial prosthetic socket 10, in one embodiment, showing supportive clamp 184 and a distal prosthetic component connection adapter 182 that is positioned offset from the center of base plate 170. The movement that has occurred, as indicated by the arrow, is that supportive clamp 184 has moved in a posterior direction with respect to base plate 170 (in a converse expression, base plate 170 has moved in an anterior direction with respect to supportive clamp 184). The relative position of supportive clamp 184 with respect distal base plate 170 as shown in FIG. 7B can be regarded as neutral, centered, or without offset from center. Notably, the default or neutral rotational position of supportive clamp 184 with respect to base plate 170 has been maintained (as shown also in FIG. 7B).

FIG. 7D shows a bottom view of a distal base assembly 130 of a transtibial prosthetic socket 10, showing a supportive clamp 184 and a distal prosthetic component connection adapter 182 that is rotationally positioned 45 degrees from neutral, as indicated by the arrow. FIG. 7E is similar to FIG. 7E except that the rotational arc has been extended; supportive clamp 184 and a distal prosthetic component connection adapter 182 are is rotationally positioned 180 degrees from neutral, as indicated by the arrow. In these views, the offset position of supportive clamp from the center of base plate 170 has not moved from the center. By a combination of the rotational capability of supportive clamp 184 and the slidable offset capability of distal connection adapter 184, it may be understood that distal prosthetic component connection adapter 182 can be positioned anywhere within a circle defined by the dimensional range defined by the offset distance range.

Referring now to distal connecting components of distal base assembly 130, in some embodiments, distal base assembly 130 includes a supportive clamp 184 disposed distal to distal base plate 170, the supportive clamp being rotatable with respect to the distal base plate. Supportive clamp 184 hosts a distal prosthetic component connection adapter 182, that can mate with a conventional 4-hole adapter or with an M36 threaded adapter that can accept male or female pyramids for coupling to distal prosthetic components.

Referring now generally to a patellar bar 30, and knee distribution pad 40, one of the challenges of facing a successful transtibial prosthetic socket is to relieve the distal end of the residual limb from bearing much weight. In transfemoral prosthetic sockets, features such as a brim and particular pelvic ischium-engaging features are used for this purpose, the ischium being especially adapted to bear weight. The anatomy of the transtibial residual limb does not have such a particularly convenient anatomy, but it does have the femoral and tibial condyles that can be put to use. Knee pressure distribution pad 40 is configured to absorb body weight, which is then transmitted through the socket, relieving the amputated distal end of the tibia from much of this burden.

FIGS. 8A-8B both show an anterior view of a proximal portion of a transtibial prosthetic socket frame 20, showing, in particular, a patellar bar 30 extending between two anterior struts 20, the patellar bar supporting a proximally-extending knee pressure distribution pad support post 34. FIG. 8B additionally a knee pressure distribution pad 40 supported on support post 34 extending proximally from a central bridging section 33 of patellar bar 30. In some embodiments, as shown, patellar bar 30 has two attachment arms 32 that connect to each of the anterior struts 20, below proximal portions 24 of the anterior struts. As seen in FIG. 8B, a mounting piece 45 that fits over mounting post 34 is sewn into knee pressure distribution pad 40. The mating aspects of mounting post 34 and mounting piece 45 are vertically adjustable, thereby allowing for the relative height of knee pressure distribution pad to vary with respect to struts 20, and accordingly, with respect to elevation above the distal base assembly of the socket.

Figure 8C:
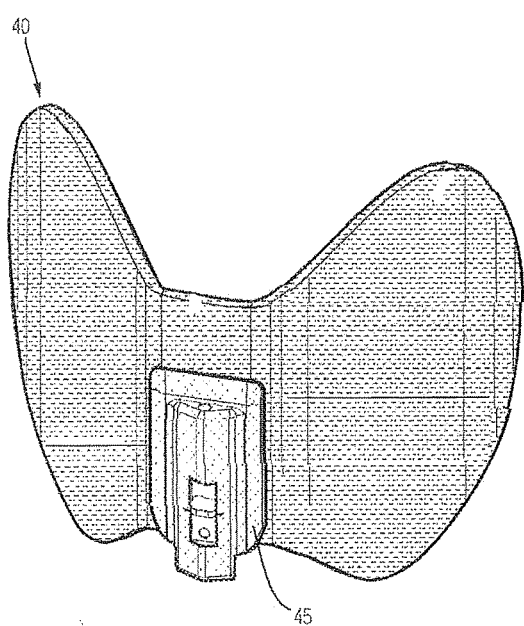
FIG. 8C is a perspective view of an isolated knee distribution pad as in FIG. 8B.
Figure 8D:
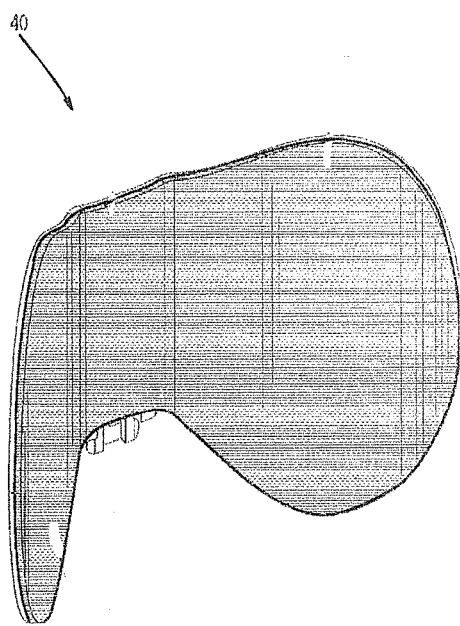
FIG. 8D is an internal side view the pad of FIG. 8C.

FIG. 8C shows an external or anterior facing view of an embodiment of an isolated knee distribution pad 40 for use in a transtibial prosthetic socket. Mounting piece 45 is seen transparently through the surface of the pad, into which the mounting piece is sewn. FIG. 8D shows an internal or posterior facing view of an embodiment of an isolated knee distribution pad for use in a transtibial prosthetic socket. When transtibial prosthetic socket 20 is hosting a transtibial residual limb, knee distribution pad 40 distributes pressure broadly across the knee, and provides a surface that captures much of body weight of the patient.

Figure 8E:
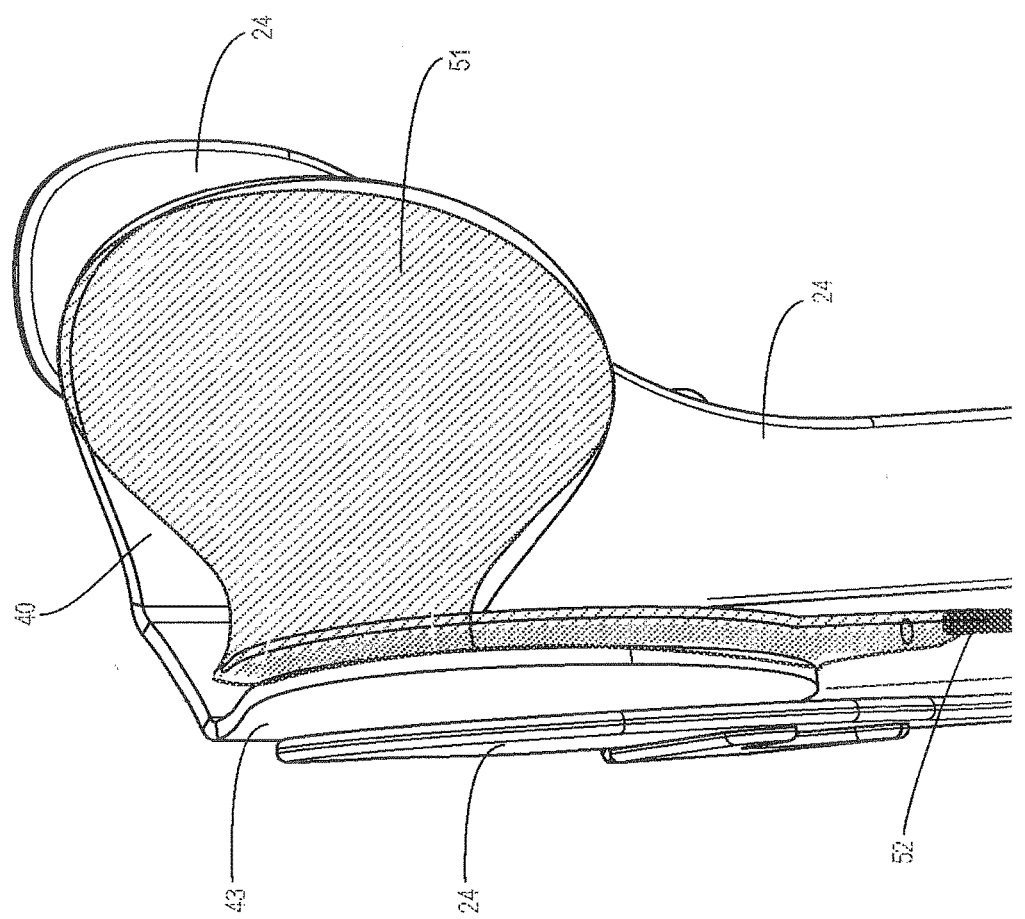
FIG. 8E is a side/anterior internal perspective view of the isolated knee distribution pad of FIGS. 8C and 8D, with an air bladder adhered to an internal aspect of the knee pressure distribution pad.
Figure 10A:
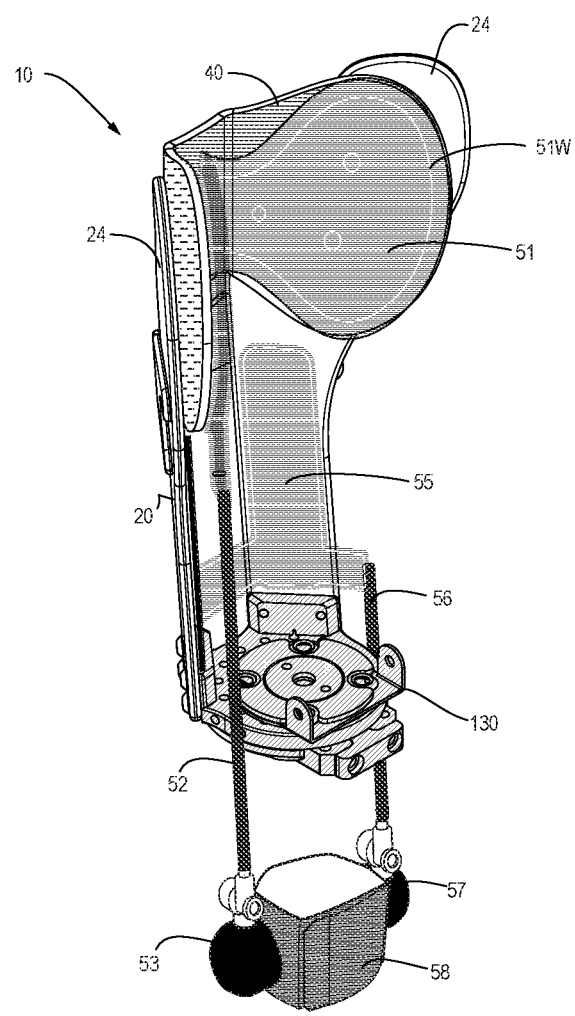
FIG. 10A is a perspective view of a transtibial prosthetic socket frame with proximal and distal bladders, according to one embodiment.
Figure 10B:
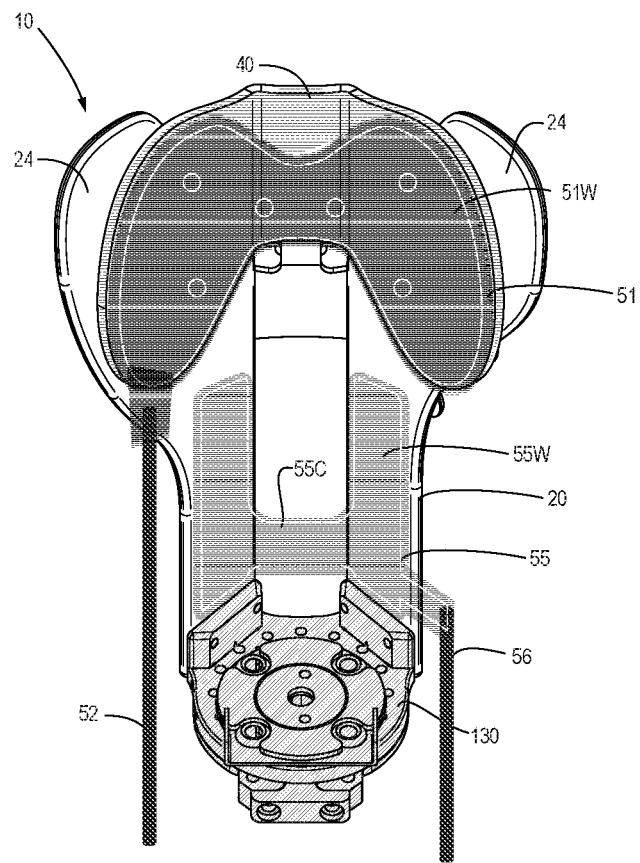
FIG. 10B is a posterior view of the transtibial prosthetic socket frame of FIG. 10A.

FIG. 8E shows a side-anterior internal perspective view of an embodiment of an isolated knee distribution pad 40 for use in a transtibial prosthetic socket with a proximal air bladder 51 adhered to an internal aspect of the knee pressure distribution pad. Some embodiments of the invention include two air bladders, this proximal air bladder 51 and distal air bladder 55, both of which are depicted in FIGS. 10A-10B, and as described in greater detail below.

Referring now generally to posterior 60 and tensioning anchor housing 70, particular embodiments of transtibial prosthetic socket 10 include twin anterior struts 20 and a single posterior strut 60. In brief overview, FIGS. 9A-9F show various views of an embodiment of a posterior strut 60, showing, in particular, views of a tensioning anchor housing 70 mounted on the proximal end of the strut. The tensioning anchor embodiment 70 includes an intra-frame force applicator 75, disposed on an internal aspect of the anchor and a rotary tensioning actuator 72 disposed on an external aspect of the anchor.

Figure 9B:
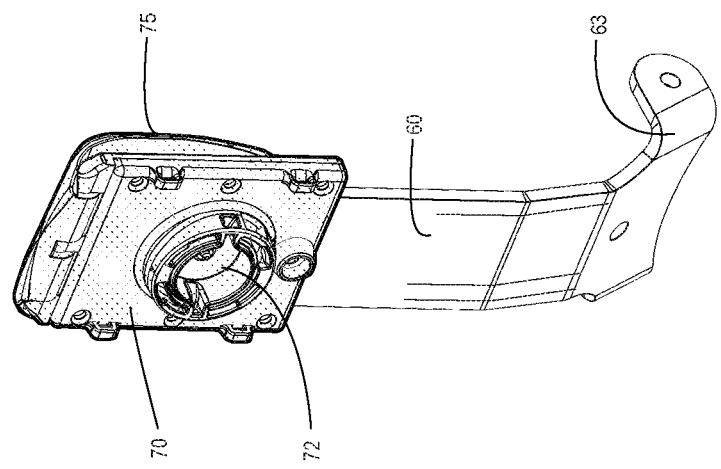
FIG. 9B is a perspective view of the strut of FIG. 9A, with a tensioning anchor housing mounted on it.
Figure 9A:
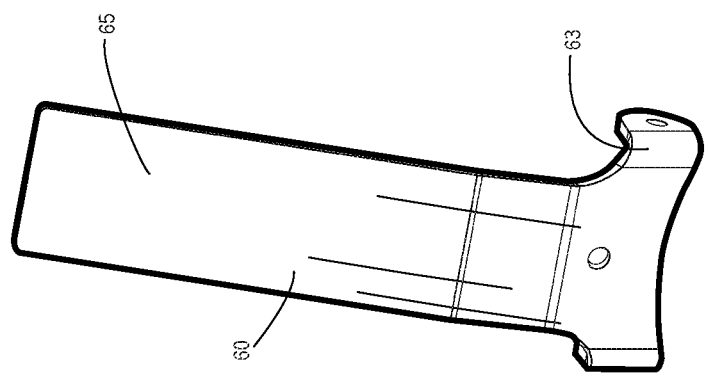
FIG. 9A is a perspective view of a posterior strut of a transtibial prosthetic socket, according to one embodiment.

FIG. 9A shows an external view of an isolated posterior strut of a transtibial prosthetic socket, showing in particular, proximal end 65 and distal hinged end 63, configured to be coupled to a movable carriage component of a distal base assembly. FIG. 9B shows an external perspective view of isolated posterior strut 60 with a tensioning anchor housing 70 mounted on the proximal end of the strut. A rotary actuator 72 is seen on the external aspect of tensioning anchor housing 70. The role of rotary actuator 72 in a tensioning system is shown in detail in FIGS. 11D-11E, and described further in that context below. An intra-frame force applicator 75 is seen on the internal aspect of tensioning anchor housing 70, and is shown in greater detail in FIGS. 9C-9F, which focus on structural details and the mechanism of the inwardly deflective movement capability of intra-frame force applicator 75. The functional purpose of intra-frame force applicator is to apply an anteriorly directed force in the popliteal region of a hosted residual limb, such capability being helpful in optimally positioning and stabilizing the residual limb within the confines of the transtibial prosthetic socket frame.

Figure 9D:
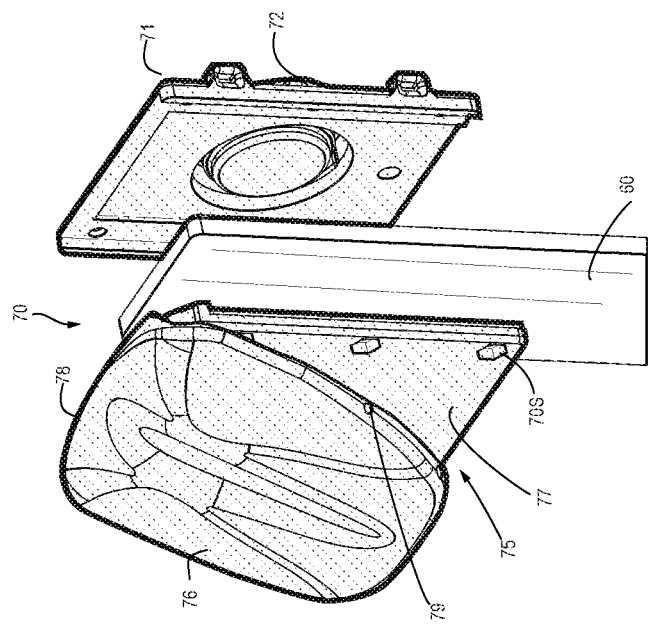
FIG. 9D is an exploded view of the tensioning anchor housing of FIGS. 9B and 9C.
Figure 9C:
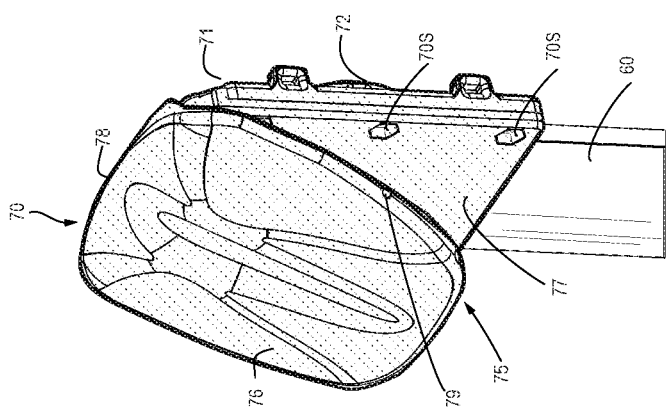
FIG. 9C is a perspective view of the tensioning anchor housing of FIG. 9B, showing an intra-frame force applicator mounted on it.

FIG. 9C shows a perspective view of tensioning anchor housing 70, which includes a deflectable flap 76 and a supportive back portion 77 that is disposed against the internal surface of posterior strut 60. Deflectable flap 76 and supportive back portion 77 are couple together by a hinged connection 78 at their respective top edges, which allows an inward deflection of deflectable flap 76 when inwardly tensioned. Deflectable flap 76 includes tension cord channels 79, whose functionality is shown later in the context of FIGS. 11D-11E and associated description of a tensioning system. The lateral sides of supportive back portion 77 has screw holes 70S that allow tensioning anchor housing 70 to be secured at a variable height on posterior strut 60. FIG. 9D shows a view similar to that of FIG. 9C, but tensioning anchor housing 70 is exploded to show a two part assembly arrangement and how it embraces the proximal end of posterior prosthetic socket 60.

Figure 9F:
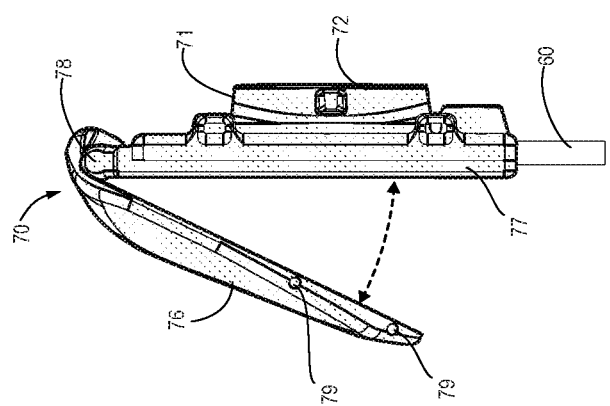
FIGS. 9E and 9F are side views of the tensioning anchor housing of FIGS. 9B-9D, in closed and open positions, respectively.
Figure 9E:
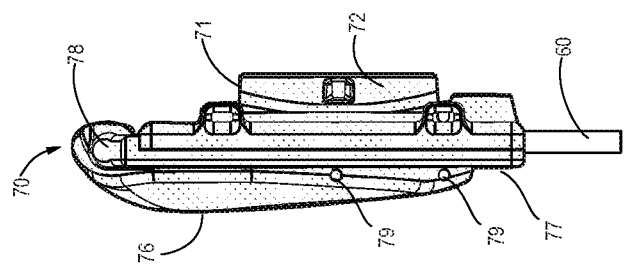

FIGS. 9E-9F show side views of tensioning anchor housing 70, showing, in particular, an intra-frame force applicator in a closed position and an open position, respectively, the arc of the opening movement being indicated by the arrow in FIG. 9F.

FIGS. 10A-10B show a perspective view and a posterior face view, respectively, of proximal bladder 51 and distal bladder 55, each as positioned within a transtibial prosthetic socket frame 10. Proximal bladder is served by air line 52 that extends distally, where it connects to proximal bladder pump unit 53. Distal bladder 55 is served by air line 56 that extends distally, where it connects to distal bladder pump unit 57. Proximal bladder pump unit 53 and distal bladder pump unit 57 are both supported by bladder support cuff 58 that is arranged around a distal prosthetic component (i.e., a prosthetic component distal to distal base assembly 130). Bladder pump units 53 and 57 are hand operable by the patient.

Proximal bladder 51 is disposed against (in some embodiments bonded or adhered to) the internal surface of knee pressure distribution pad 40 (seen previously in FIG. 8E); it includes broadened lateral wings 51C (generally congruent in outline to the shape of knee pressure distribution pad 40) and a central section 51C that connects wings 51W. Distal bladder 55 is disposed against the internal surface of distal portions of anterior struts 55; it includes vertically elongate wings 55C and a central section 55C that connects wings 55C. The sizes and shapes of bladder embodiments may assume any suitable configuration, and may, in some embodiments be conjoined.

The function of bladders 51 and 55 is to allow adjusting of the residual limb hosting volume within the confines of the cavity defined by transtibial prosthetic frame 10, and to place control over that hosting volume in the hands of the patient. Notably and advantageously, air pressures within bladders 51 and 55 are independently controllable, allowing a greater level of individualized intra-frame cavity volume control than would be provided by a single bladder. Taken together, the relative degree of inflation of bladders 51 and 55 represent one of several approaches to customizing the shape and volume of the residual limb hosting cavity of transtibial prosthetic socket 10 in order to custom fit the particular size and shape of a patient's residual limb. More particularly, controlling the pressure in bladders 51 and 55 is in the hands of the patient, and may easily be adjusted during the day, according the preference of the patient.

FIGS. 11A-11E show various views of an embodiment of transtibial prosthetic socket tensioning system 69, which includes a tensioning anchor housing 70, a rotary tensioning actuator 72, a tensioning cable 74, an intra-frame force applicator 75, and a tensioning strap 43, Patellar bar 30 and portions of anterior struts 20 are also involved in socket tensioning The rotary actuator provided by Boa Technology (Denver Colo.) is an example of an embodiment of rotary tensioning actuator 72.

Figure 11A:
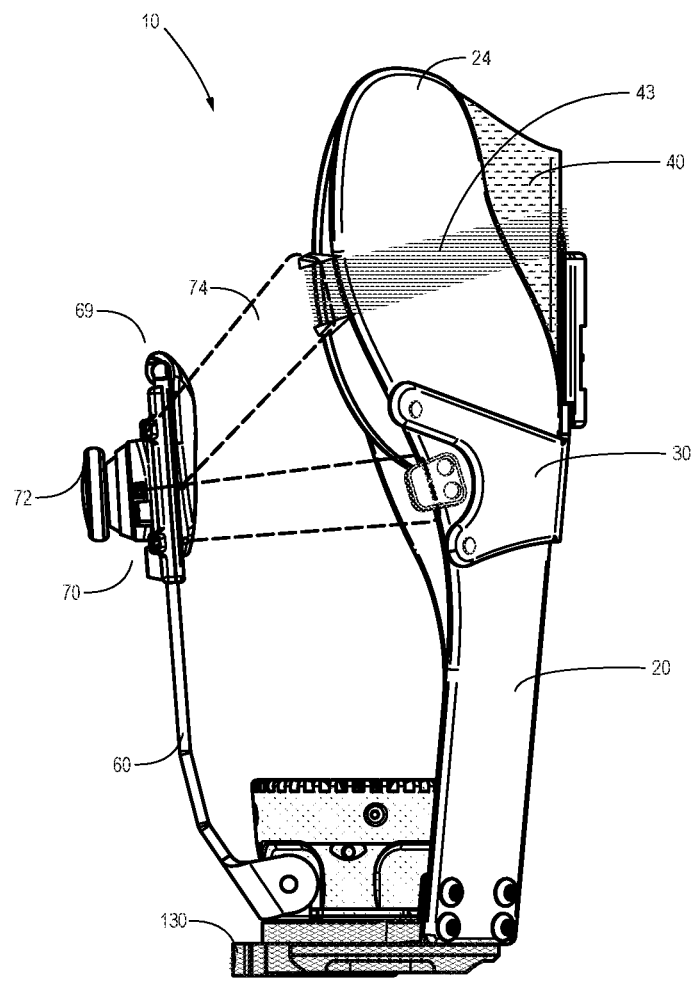
FIG. 11A is a side view of a transtibial prosthetic socket rigged with a tensioning system, according to one embodiment.
Figure 11B:
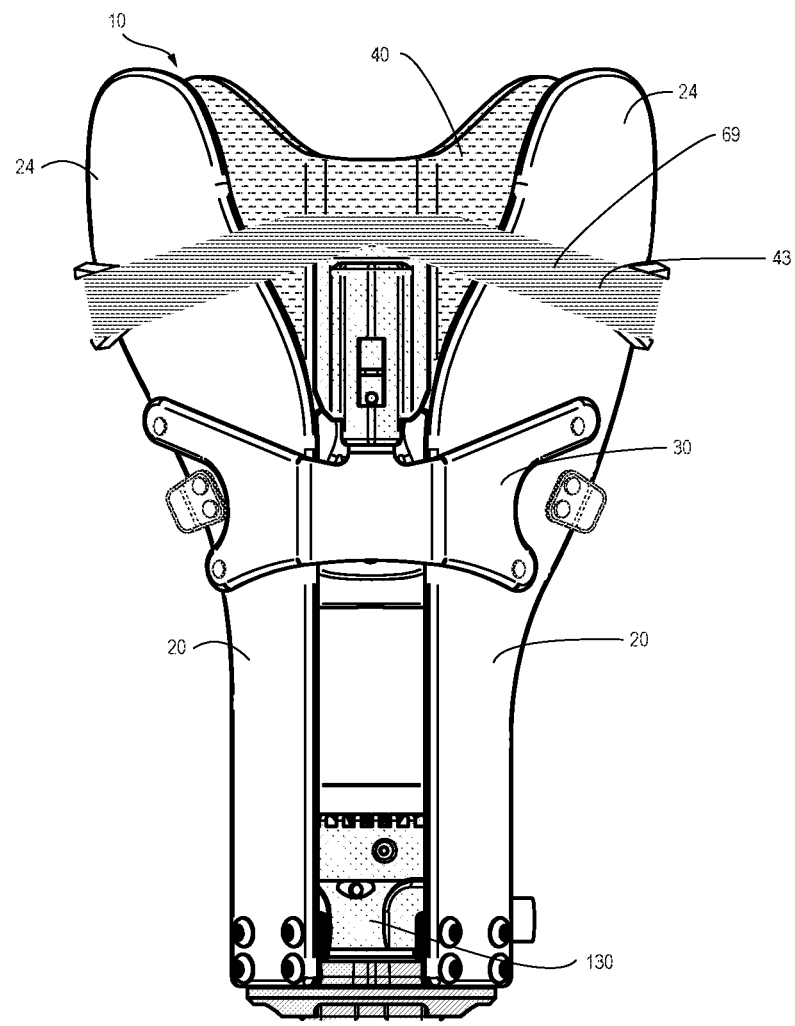
FIG. 11B is an anterior view of the transtibial prosthetic socket of FIG. 11A.

FIGS. 11A-11B show a side view and anterior face view, respectively, of a transtibial prosthetic socket frame 10 rigged with tensioning system 69. Tensioning cable 74 is one continuous line, with both ends terminating in rotary tensioning actuator 72. The effect of cranking rotary tensioning actuator is lengthen or shorten the total amount of cable length in play; such variation in length plays throughout the path of tensioning cable 74. As shown in FIG. 11A, tensioning system 69 is in a state of relative repose; the total length of tensioning cable in play is relatively long. In contrast, tensioning system is in a state of heightened tension in FIG. 11C.

Figure 11C:
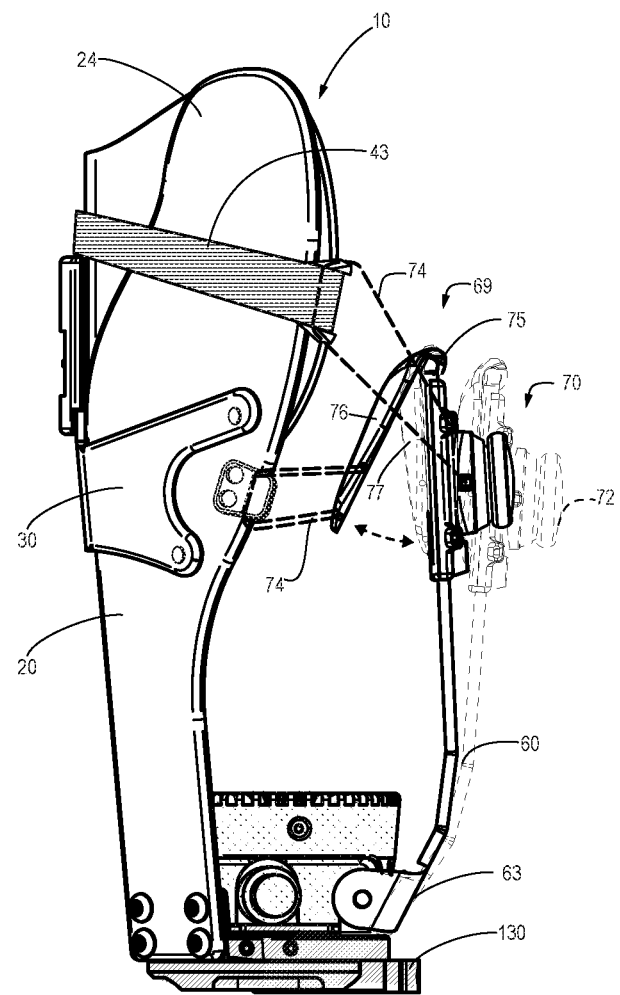
FIG. 11C shows a lateral view of the transtibial prosthetic socket of FIGS. 11A and 11B, with the tensioning system activated.

FIG. 11C shows an anterior face view of a transtibial prosthetic socket 10 rigged with a tensioning system 69, the tensioning within system 69 being activated. Effects created by this tensioning include the inward pull on posterior strut 60 (as shown by the ghosted representation of strut 60 in repose), and an inward deflection of deflectable flap 76 of intra-frame force applicator 75 (all included within tension anchor housing 70). A better view of this aspect of activation of the tensioning system is provided in FIGS. 9E-9F.

Figure 11D:
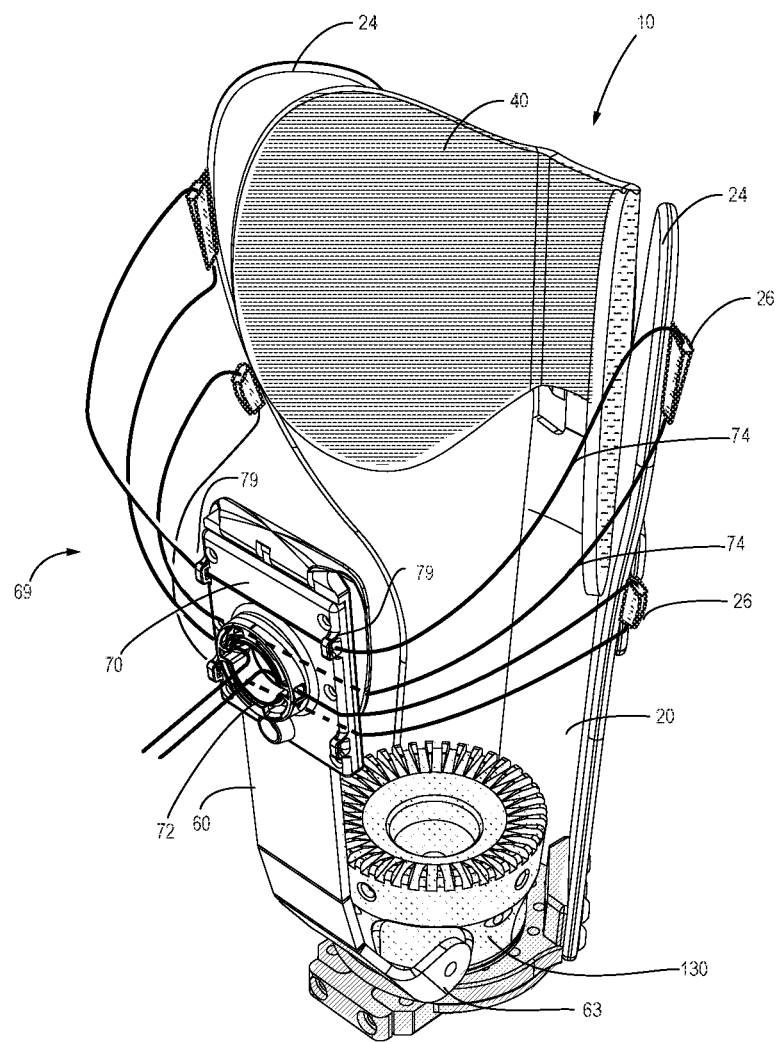
FIG. 11D is a top perspective view of the transtibial prosthetic socket of FIGS. 11A-11C, with a portion of the socket frame ghosted to accentuate visibility of the tensioning cable arrangement.

FIG. 11D shows a top perspective view of a transtibial prosthetic socket 10 rigged with a tensioning system, a major portion of the socket frame being ghosted to accentuate visibility of the arrangement of tensioning cable 74. Cable 74 laces back and forth between tensioning anchor housing 70 (through cable channels 79) and proximal and distal sites on the proximal portion 24 of struts 20, as threaded through cable guides 26.

Figure 11E:
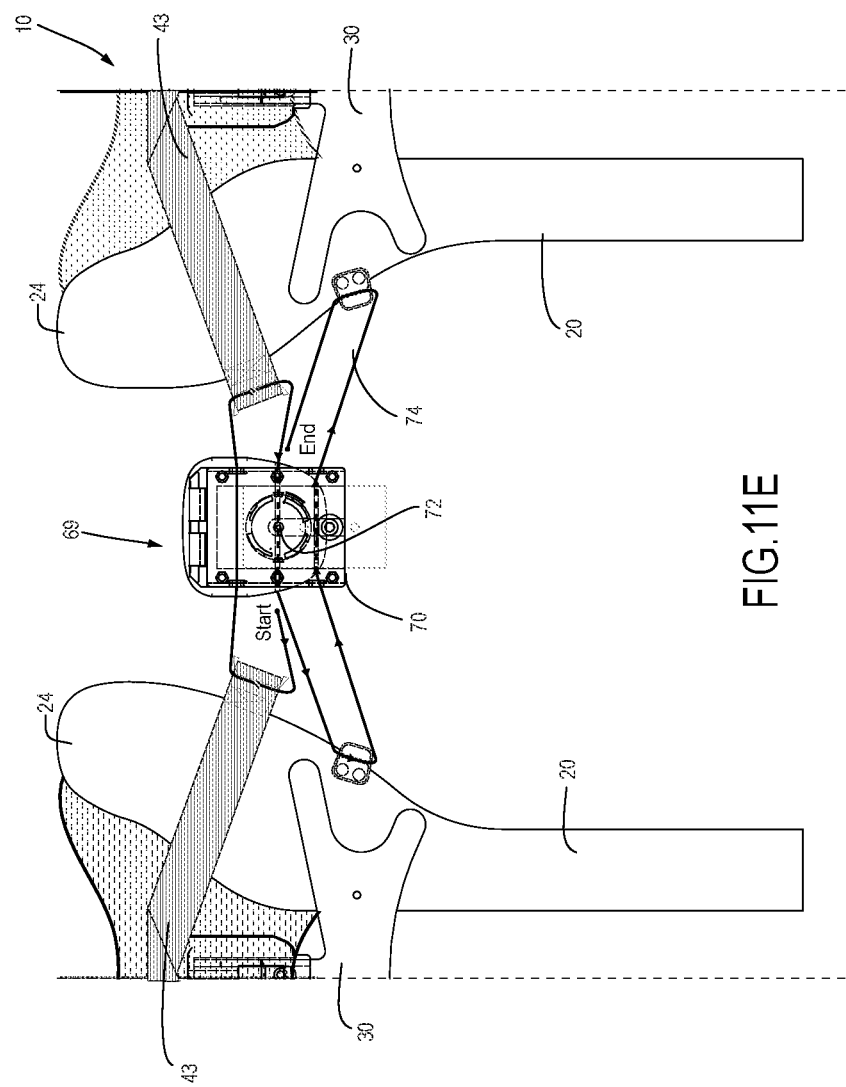
FIG. 11E is an anterior flattened face view of the transtibial prosthetic socket of FIGS. 11A-11D, showing the arrangement of the cable rigging through the tensioning anchor housing and cable connections to anterior struts and a strap arranged around the anterior struts.

FIG. 11E shows an anterior flattened face view of a transtibial prosthetic socket 10 rigged with tensioning system 69, showing in particular, the arrangement of tensioning cable 74 as rigged through the tensioning anchor housing 70 and cable connections to anterior struts 20 and a strap 43 arranged around anterior struts 20.

FIGS. 11D and 11E show the tensioning path defined by tensioning cable 74 in the most detail. Tensioning cable has two termini, terminus 74A and terminus 74B. Terminus 74A and terminus 74B are both disposed within tensioning anchor 70 and connected to a rotatable dial within the tensioning anchor such that cable 74 is pulled from both termini when tension is applied to cable 74.by manual cranking of the rotary actuator 72. The path of cable 74 has broad left-right or lateral-medical symmetry; for narrative purposes, the description will proceed from terminus 74A to 74B.

Accordingly (and with particular reference to FIG. 11E), proceeding from terminus 74A, cable 74 loops through a cable guide 78 on one end 43A of tensioning strap 43. From there, cable 74 proceeds back to and through tensioning anchor 70, and from there to a cable guide 78 on a second end 43B of tensioning strap 43, looping therethrough. From there, cable 74 proceeds back to and through tensioning anchor 70, proceeding thence to a cable guide 26 mounted on a posterior edge of one of the two anterior struts 20, looping therethrough. From there, cable 74 proceeds back toward tensioning anchor 70, extending through a channel 78 disposed across the lower edge 77 of intra-frame force applicator 75. From there, cable 74 proceeds to a cable guide 26 mounted on a posterior edge of second of the two anterior struts 20, looping therethrough. From there, cable 74 proceeds back to tensioning anchor 70, where it attaches to a site on the rotary surface of rotary actuator 72.

As rotary actuator 72 is cranked by a patient, the effective length of cable 74 is shortened, the shortening of such length distributed with substantial proportionality through the entirety of the path of cable 74, as described above. Rotary actuator 70 is configured such that cranking the rotary dial in the tensioning direction fixes the position of the dial in a ratchet like manner, stabilizing the tension in cable 74. A release mechanism within rotary actuator 70, manually triggered, releases the dial and cable 74 passively returns to an untensioned state.

FIGS. 12A-12C show various views of fabric jacket 200 configured to fit over and within a transtibial prosthetic socket frame 10. FIG. 12A shows an anterior view of a prosthetic socket jacket 200 as arranged over transtibial prosthetic socket frame 10, and FIGS. 12B and 12C provide posterior face view and a lateral face view, respectively.

Fabric jacket 200 includes a lining or central tubular section 210 and exterior section 220. Jacket lining 210 includes a proximal edge 211, a distal edge 212, two frame suspension pockets 214 disposed on proximal edge 211, and frame suspension pockets 214 may contain thermoplastic inserts.

Figure 13:
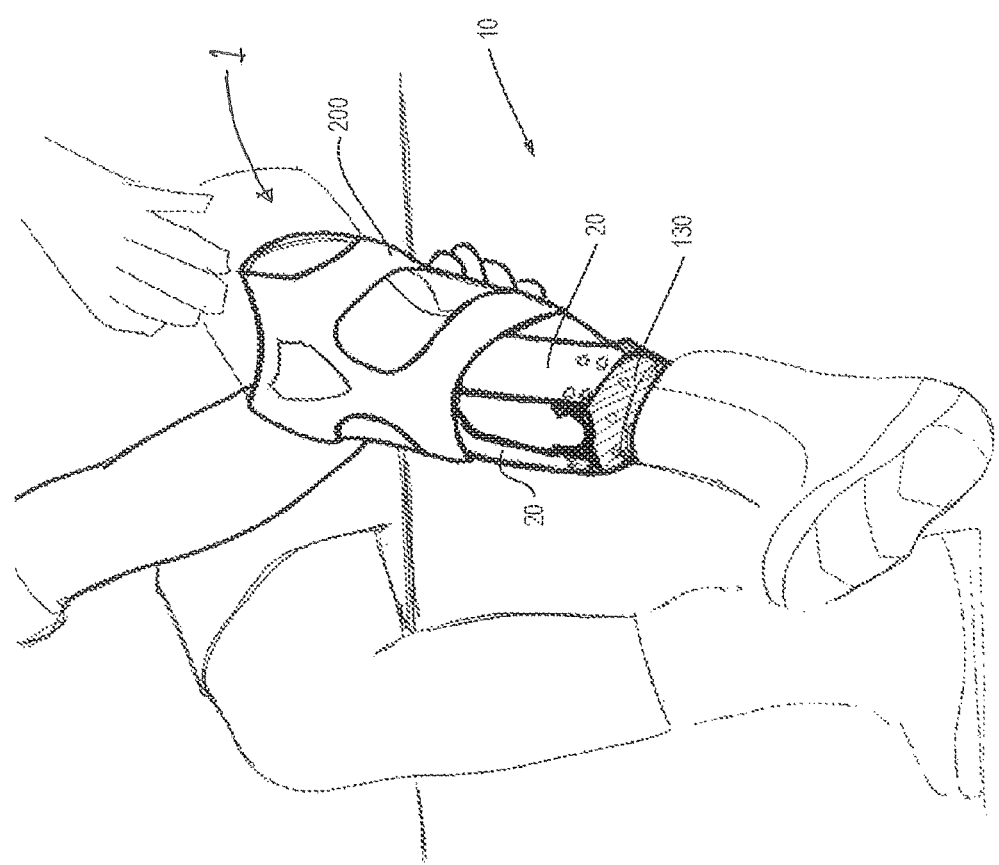
FIG. 13 is a view of a transtibial prosthetic socket user donning a socket, and adjusting a rotary actuator for a tensioning mechanism.

FIG. 13 shows a view of a transtibial prosthetic socket user 1 donning a transtibial prosthetic socket 10, and adjusting a rotary actuator positioned on the proximal strut for a tensioning mechanism to adjust level of tension around the set of struts to an appropriate level of tension.

Figure 14:
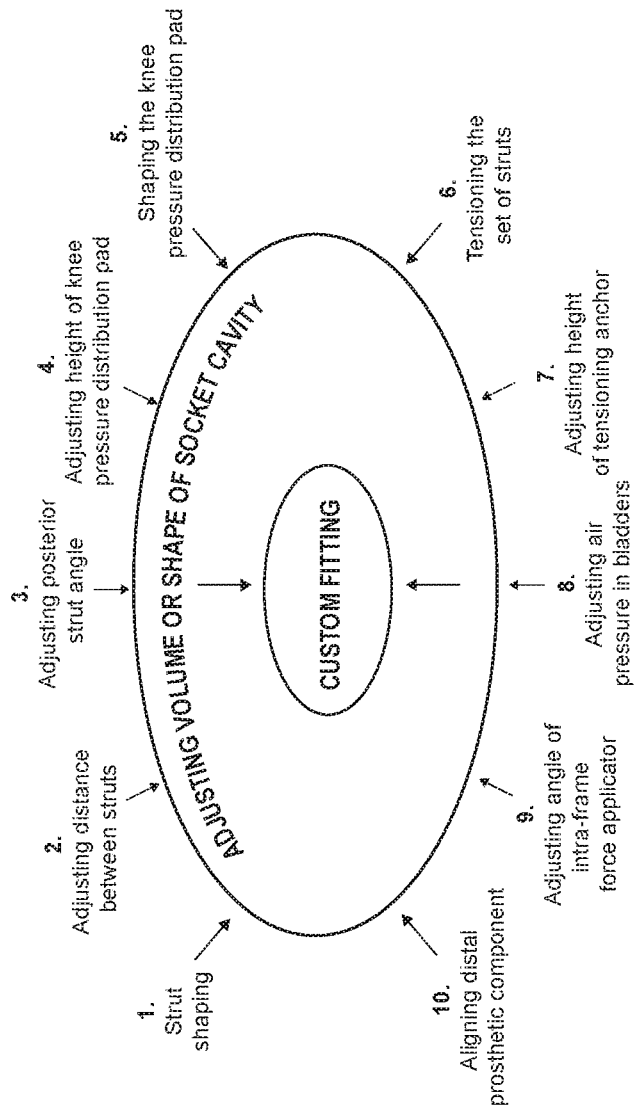
FIG. 14 is a schematic diagram of various methods by which structural features of a transtibial prosthetic may be used to adjust the volume and/or shape of a prosthetic socket cavity, and thereby provide a custom fit for a patient, according to various embodiments.

FIG. 14 is a schematic diagram of various methods by which structural features of a transtibial prosthetic, per provided embodiments, can adjust the volume or shape of a prosthetic socket cavity, and thereby provide a custom fit for a patient.

Embodiments of the invention include methods of supporting the residual transtibial limb of a patient by way of a prosthetic socket 10, and more particularly, for adjusting the fit of the prosthetic socket on the residual limb to an optimal state. A number of method embodiments are directed to adjusting fit by way of adjusting the residual limb hosting volume within a transtibial socket, as determined generally by the configuration of longitudinal struts arising from a distal base. In some embodiments, the shape of the volume can have particular significance for the quality of the fit; accordingly, in some embodiments, adjusting the fit may include adjusting the shape of the residual limb hosting volume. Components of an inventive transtibial prosthetic socket 10 are described elsewhere.

Methods of supporting the residual limb and adjusting the fit of the prosthetic socket may occur by any of several approaches, as depicted schematically in FIG. 13. Embodiments of a transtibial prosthetic socket 20 have a multitude of adjustable features, as have been described above. Each of these features, by their adjustments may adjust the volume or shape of the prosthetic socket cavity, or alter the disposition of the residual limb within the socket, or alter the disposition of the residual limb within the socket in relation to the patient's body or in relation to distal prosthetic components, or some combination of these various functionalities. By such functionalities, further, each of these adjustments may contribute to an aspect of custom fitting the transtibial prosthetic socket to the individual patient.

Prior to a describing these methods in detail, as below, a non-limiting list of these various adjustments can be enumerated as follows:

1. Shaping one or more of the anterior struts 20 or posterior strut 60 to conform to the conformation of the residual limb.
2. Adjusting the distance between anterior struts 20 (as a unit) and posterior strut 60 at the level of the distal base assembly 130.
3. Adjusting the angle of posterior strut 60 with respect to distal base assembly 130 by way of the hinged connection 63.
4. Adjusting the height of knee pressure distribution pad 40 with respect to the anterior struts 20 or the distal base assembly 130.
5. Shaping the knee pressure distribution pad 40 by way of thermal reforming of a thermoplastic layer of the pad.
6. Adjusting the tensioning around the set of struts (anterior struts 20 and posterior strut 60) by way of any of the multiple features of tensioning mechanism 69.
7. Adjusting the height of the tensioning anchor housing 70 on the posterior strut 60,
8. Adjusting the air pressure in one or both of the bladders (proximal bladder 51 or distal bladder 55.
9. Adjusting the angle of intra-frame force applicator 75 associated with the tensioning anchor housing 70.
10. Aligning a distal prosthetic component by way of adjustments within components of the distal base assembly 130.

In some embodiments, supporting the residual limb and adjusting the fit of a prosthetic socket may occur by way of altering one or more contours of any of the struts within the described set of struts. Typical embodiments of the struts are formed from a thermoplastic fiber composite material. With such a composition, struts may be contoured by warming a one or more of the struts, or a portion of any strut, to a sufficient temperature and for a sufficient time that the strut becomes malleable, and then reshaping the malleable strut to include one or more desired contours such that the fit of the prosthetic socket on the transtibial residual limb is improved.

As noted above, supporting the residual limb and adjusting the fit a prosthetic socket may occur by way of adjusting a residual limb hosting volume of the prosthetic socket cavity. As an alternative to volume per se, the size of the prosthetic socket cavity may be expressed in terms such as diameter or circumference, which can vary along the central longitudinal axis of the socket. Further, as noted above, volume can have a shape, and accordingly, adjusting volume may include adjusting the shape of the space defined by such volume.

Adjusting the residual limb hosting volume may occur by any one or more of several approaches. In one approach, it may occur by adjusting a distance between (a) the anterior struts, as a unit, and (b) the posterior strut at the distal base assembly. In some embodiments, adjusting this distance between the anterior struts and the posterior strut occurs by way of moving a carriage the supports the posterior strut with respect to a base plate the supports the anterior struts.

In a second approach to adjusting the residual limb hosting volume, such may occur by adjusting an angle of the posterior strut with respect to the distal base assembly. Embodiments of the posterior strut are connected to the distal base assembly by way of hinge. When the posterior strut is at a vertical or substantially vertical angle, the residual limb hosting volume is at a relative minimum. As the hinged angle of the posterior strut is adjusted outward, the limb hosting volume increases over that relative minimum.

In a third approach, to adjusting the residual limb hosting volume, such may occur by adjusting the level of tension applied to the set of struts by a tensioning mechanism configured to press the struts toward the center of the residual limb hosting volume.

In some embodiments, supporting the residual limb and adjusting the fit a transtibial prosthetic socket may occur by way adjusting the height or the elevation of a tensioning anchor above a distal base assembly. As described elsewhere, in some embodiments of transtibial prosthetic socket, an anchor for a circumferential tensioning system may be positioned on a strut, such as a posterior strut. Adjusting the height of the circumferential tensioning anchor with respect to the distal base assembly may have any one or more of several consequences, such as adjusting the lengthwise fit of the transtibial prosthetic socket on the residual limb, or adjusting the shape of the space defined by the prosthetic socket cavity.

In some embodiments, supporting the residual limb and adjusting the fit a transtibial prosthetic socket may occur by way adjusting the height or the elevation of a knee pressure distribution pad above a distal base assembly. As described elsewhere, in some embodiments of transtibial prosthetic socket, knee pressure distribution pad may be supported by anterior struts on a height adjustable mechanism. Adjusting the height of the knee pressure distribution pad with respect to the distal base assembly may have any one or more of several consequences, such as adjusting the lengthwise fit of the transtibial prosthetic socket on the residual limb, or adjusting the shape of the space defined by the prosthetic socket cavity In some embodiments, supporting the residual limb and adjusting the fit a prosthetic socket may occur by way custom shaping of the knee pressure distribution pad so as to particular optimize the fit of the pad around the patella and condyle regions of the knee. As described elsewhere, some embodiments of a knee pressure distribution pad including a layer of thermoplastic fiber composite material. In such embodiments, a method of supporting a residual limb may include warming the knee pressure distribution pad or a portion thereof to a sufficient temperature and for a sufficient time that the knee pressure distribution pad becomes malleable, and then shaping the knee pressure distribution pad to include one or more desired contours such that the fit of the prosthetic socket on the transtibial residual limb is improved.

In some embodiments of a transtibial prosthetic socket, a knee pressure distribution pad supports a proximal fluid bladder on an interior aspect of the knee pressure distribution pad, and accordingly, in which instance, reshaping the knee pressure distribution pad effectively includes a custom shaping of the proximal fluid bladder.

In some embodiments, supporting the residual limb and adjusting the fit a prosthetic socket may occur by way of adjusting the residual limb hosting volume within the boundaries defined by the set of struts and the distal base assembly. Accordingly, adjusting the residual limb hosting volume may occur by way of adjusting the level of air pressure in one or more air bladders disposed within the prosthetic socket frame. Some particular prosthetic socket embodiments have two air bladders, in which case, adjusting the residual limb hosting volume may include adjusting the level of air pressure in each of the bladders, and in some embodiments, adjusting the level of air pressure in the two air bladders may be independently performed.

Dome embodiments of a transtibial prosthetic socket include a deflectable intra-frame force applicator mounted on a prosthetic socket strut, as described elsewhere herein. In such embodiments, supporting the residual limb and adjusting the fit of a transtibial prosthetic socket may occur by way of adjusting the angle of a deflectable intra-frame force application. More particularly, an inwardly deflectable intra-frame force applicator may be drawn into the cavity of the prosthetic socket, for example, in an anterior direction, by use of tensioning cable connected to a distal portion of the deflectable intra-frame force applicator. Typically, this tensionable actuation occurs when circumferential tension is being applied to the proximal portion of a prosthetic socket, as a whole, and the effect of the inward deflection of the intra-frame force applicator is to engage the popliteal region of the residual limb, pressing in an anterior and/or upward direction.

In some embodiments, supporting the residual limb and adjusting the fit a prosthetic socket may occur by way of adjusting the alignment of a distal prosthetic component with respect to the central longitudinal axis of the prosthetic socket. Having a biomechanically correct alignment of a distal prosthetic component with respect to the prosthetic socket is an important quality of supporting the transtibial prosthetic limb. In one approach to adjusting alignment, the distal prosthetic component connecting adapter may be rotated with respect to the central longitudinal axis of the prosthetic socket. Inasmuch as a distal prosthetic component is directly connected to the distal prosthetic component connecting adapter, any offset movement or rotational movement of the adapter translates into an offset or rotation of the distal prosthetic component.

In a second approach to adjusting alignment, the position of the center of a distal prosthetic component connecting adapter within the distal base assembly can be moved such that the center of the adapter is offset with respect to the central longitudinal axis of the prosthetic socket.

Any one or more features of any embodiment described herein may be combined with any one or more other features of any other embodiment, without departing from the scope of the invention. Further, the invention is not limited to the embodiments that are described or depicted herein for purposes of exemplification, but is to be defined only by a fair reading of claims appended to the patent application, including the full range of equivalency to which each element thereof is entitled. Further, while some theoretical considerations have been offered to provide an understanding of the technology (e.g., the effectiveness of a positioning slings in improving biomechanical control of the residual limb by acting on the residual bone as a lever), the claims are not bound by such theory.

The invention claimed is:

1. A prosthetic socket for a transtibial residual limb of a patient comprising:
   a prosthetic socket frame, the frame comprising:
      a distal base assembly, comprising:
         a base plate;
         a carriage disposed proximal to the base plate, the carriage configured to support a prosthetic socket suspension arrangement; and
         a distal prosthetic component connection adapter distal to the base plate, wherein the connection adapter is rotatable with respect to the base plate, and moveable with respect to the base plate between a position aligned with the prosthetic socket's central longitudinal axis and a position offset from the socket's central longitudinal axis; and
      multiple struts, each of the struts attached to the distal base assembly at its respective distal end, the multiple struts comprising:
         a medial anterior strut;
         a lateral anterior strut; and
         a posterior strut,
      wherein the multiple struts and the distal base assembly, collectively, define a prosthetic socket cavity comprising a central longitudinal axis and a residual limb hosting volume,
      wherein the residual limb hosting volume of the prosthetic socket cavity is configured to be adjustable by way of an adjustment of a variable anterior-posterior position of the carriage with respect to the distal base plate.

2. The prosthetic socket of claim 1, wherein the multiple struts comprise a thermoplastic fiber composite material, the fiber of the composite material comprising a continuous fiber.

3. The prosthetic socket of claim 1, wherein the multiple struts consist of composite material with thermoplastic fibers, the fibers of the composite material consisting of continuous fibers.

4. The prosthetic socket of claim 1, wherein the multiple struts are custom molded to conform to contours of an individual transtibial residual limb.

5. The prosthetic socket of claim 1, wherein the suspension arrangement comprises a prosthetic socket liner that is connected to the distal base assembly by way of a pin lock mechanism.

6. The prosthetic socket of claim 1, wherein the suspension arrangement comprises a prosthetic socket liner that is suspended on the residual limb by way of a suction mechanism.

7. The prosthetic socket of claim 1, wherein the distal base assembly comprises a distal prosthetic component connector that comprises a supporting clamp into which the distal prosthetic component connection adapter is seated, the connection adapter comprising a center.

8. The prosthetic socket of claim 1, wherein the posterior strut is connected to the distal base assembly by a hinged mechanism.

9. The prosthetic socket of claim 1, further comprising a tensioning mechanism configured to adjustably apply inwardly directed pressure on the set of struts, the tensioning mechanism comprising:
- a tensioning anchor housing;
- a tensioning actuator mounted on the tensioning anchor housing; and
- at least one tensioning cable arranged to connect the tensioning anchor housing and
- tensioning cable guides mounted on the set of struts.

10. The prosthetic socket of claim 1, further comprising a tensioning mechanism configured to adjustably apply inwardly directed pressure on the set of struts by way of a circumferentially arranged tensioning path followed by a tensioning cable, the path comprising:
- an origin and termination at a tensioning anchor housing mounted on the posterior strut; one or more cable guides coupled to edges of proximal aspects of each of the anterior struts; and
- a tensioning strap arranged externally around the two anterior struts.

11. The prosthetic socket of claim 1, further comprising an intra-frame force applicator disposed on an internal aspect of the posterior strut, the intra-frame force applicator configured to apply an inwardly directed pressure on the residual limb when tensioned.

12. The prosthetic socket of claim 1, wherein each anterior strut comprises a proximal clasping portion that extends posterior-ward and is contoured to conform to the residual limb.

13. The prosthetic socket of claim 1, wherein the prosthetic socket frame further comprises a patellar bar connecting the two anterior struts.

14. The prosthetic socket of claim 13, wherein the patellar bar comprises a proximally directed mounting post that is configured to support a knee pressure distribution pad.

15. The prosthetic socket of claim 1, further comprising one or more air bladders positioned within the prosthetic socket frame and configured to interface between the frame and the residual limb of the patient.

16. The prosthetic socket of claim 1, further comprising two or more air bladders positioned internal to the prosthetic socket frame, the air pressure within each of the two or more air bladders being controllable by inflation and deflation, and wherein the air pressure within each of the two or more air bladders is controllable independently of the other one or more air bladders.

17. The prosthetic socket of claim 1, wherein a proximal portion of each of the anterior struts, a patellar bar supported by the anterior struts, and the posterior strut, together, are configured to be compressed together by a tensioning mechanism.

18. The prosthetic socket of claim 1, wherein the residual limb hosting volume of the prosthetic socket cavity can be adjusted to optimize fitting the residual limb by way of a thermal reforming adjustment of the contours of any of the anterior or posterior struts.

19. The prosthetic socket of claim 1, further comprising one or more tensioning cables arranged to effect a compression of the struts, and wherein a volume of the prosthetic socket cavity can be adjusted to optimize fitting the residual limb by way of an adjustment of the tension of tensioning cables.

20. The prosthetic socket of claim 1, further comprising a fabric jacket comprising a central tubular section configured to be positioned internal to the set of struts and an exterior section configured to be positioned external to the set of struts, the central tubular portion and the external sections joined at their respective proximal edges.

21. A prosthetic socket for a transtibial residual limb of a patient comprising:
- a prosthetic socket frame, the frame comprising:
  - a distal base assembly, comprising:
    - a base plate;
    - a carriage disposed proximal to the base plate, the carriage configured to support a prosthetic socket suspension arrangement; and
    - a distal prosthetic component connection adapter distal to the base plate, wherein the connection adapter is rotatable with respect to the base plate, and moveable with respect to the base plate between a position aligned with the prosthetic socket's central longitudinal axis and a position offset from the socket's central longitudinal axis; and
  - multiple struts, each of the struts attached to the distal base assembly at its respective distal end, the multiple struts comprising:
    - a medial anterior strut;
    - a lateral anterior strut; and
    - a posterior strut,
- wherein the multiple struts and the distal base assembly, collectively, define a prosthetic socket cavity comprising a central longitudinal axis and a residual limb hosting volume,
- wherein the carriage and the base plate are moveable with respect to each other along an anterior-posterior axis, the movability providing an adjustment of the residual limb hosting volume.

22. A prosthetic socket for a transtibial residual limb of a patient comprising:
- a prosthetic socket frame, the frame comprising:
  - a distal base assembly, comprising:
    - a base plate;
    - a carriage disposed proximal to the base plate, the carriage configured to support a prosthetic socket suspension arrangement; and
    - a distal prosthetic component connection adapter distal to the base plate,
  - wherein the connection adapter is rotatable with respect to the base plate, and moveable with respect to the base plate between a position aligned with the prosthetic socket's central longitudinal axis and a position offset from the socket's central longitudinal axis; and
  - multiple struts, each of the struts attached to the distal base assembly at its respective distal end, the multiple struts comprising:
    - a medial anterior strut;
    - a lateral anterior strut; and
    - a posterior strut,
- wherein the multiple struts and the distal base assembly, collectively, define a prosthetic socket cavity comprising a central longitudinal axis and a residual limb hosting volume,
- wherein the distal base assembly further comprises:
  - a locking nut disposed proximal to the carriage;
  - a through slot comprising an anterior-posterior alignment within the base plate and a sliding dovetail piece disposed therein; and
  - one or more bolts that pass through the carriage, connecting the locking nut to the sliding dovetail piece,
- wherein the carriage and the base plate are moveable with respect to each other when the one or more bolts are loose, and wherein the carriage and the base plate are fixed in position relative to each other when the one or more bolts are tight.

23. A prosthetic socket for a transtibial residual limb of a patient comprising:

a prosthetic socket frame, the frame comprising:

a distal base assembly, comprising:

a base plate;

a carriage disposed proximal to the base plate, the carriage configured to support a prosthetic socket suspension arrangement; and a distal prosthetic component connection adapter distal to the base plate, wherein the connection adapter is rotatable with respect to the base plate, and moveable with respect to the base plate between a position aligned with the prosthetic socket's central longitudinal axis and a position offset from the socket's central longitudinal axis; and multiple struts, each of the struts attached to the distal base assembly at its respective distal end, the multiple struts comprising:

a medial anterior strut;

a lateral anterior strut; and a posterior strut, wherein the multiple struts and the distal base assembly, collectively, define a prosthetic socket cavity comprising a central longitudinal axis and a residual limb hosting volume, further comprising a knee pressure distribution pad mounted on a mounting post supported by a patellar bar arranged between the two anterior struts, wherein the knee pressure distribution pad is positioned internal to the anterior struts.

* * * * *